US006190914B1

(12) United States Patent
Grivell et al.

(10) Patent No.: US 6,190,914 B1
(45) Date of Patent: Feb. 20, 2001

(54) METHODS FOR MODULATING METABOLIC PATHWAYS OF MICRO-ORGANISMS AND MICRO-ORGANISMS OBTAINABLE BY SAID METHODS

(75) Inventors: Leslie Alan Grivell; Maarten Joost Teixeira De Mattos, both of Amsterdam; Jolanda Blom, Ouderkerk a/d Amstel, all of (NL)

(73) Assignee: Universiteit van Amsterdam, Amsterdam (NL)

(*) Notice: Under 35 U.S.C. 154(b), the term of this patent shall be extended for 0 days.

(21) Appl. No.: 09/319,989
(22) PCT Filed: Dec. 12, 1997
(86) PCT No.: PCT/NL97/00688
    § 371 Date: Jun. 14, 1999
    § 102(e) Date: Jun. 14, 1999
(87) PCT Pub. No.: WO98/26079
    PCT Pub. Date: Jun. 18, 1998

(30) Foreign Application Priority Data

Dec. 12, 1996 (EP) .................................................. 96203520

(51) Int. Cl.[7] .................................................. C12N 15/74
(52) U.S. Cl. ............... 435/483; 435/254.11; 435/254.21
(58) Field of Search ............................. 435/483, 254.21, 435/252.3, 254.11

(56) References Cited

PUBLICATIONS

Nehlin et al., The EMBO J. 9(9):2891–2898 (1990).*
Forsburg et al., Genes & Development 3(8):1166–1178 (1989).*
Bourgarel et al., Molecular Microbiology 31(4):1205–1215 (1999).*
Ronne, Trends in Genetics 11(1):12–17 (1995).*
Brown, T. A., et al., "Strain–Dependent Variation in Carbon Source Regulation of Nucleus–Encoded Mitochondrial Proteins of Saccharomyces Cerevisiae," *Journal of Bacteriology*, (1995) 177(5):1380–2.
Dang, V., et al., "A Genetic Screen to Isolate Genes Regulated by the Yeast CCAAT–Box Binding Protein Hap2p," *Yeast*, (1994) 10:1273–83.
De Winde, J. H., et al., "Global Regulation of Mitochondrial Biogenesis in Saccharomyces Cerevisiae," *Progress in Nucleic Acid Research and Molecular Biology*, (1993) 46:51–91.
De Winde, J., et al., "Global Regualtion of Mitochondrial Biogenesis in Saccharomyces Cerevisiae: ABFI and CPFI Play Opposite Roles in Regualting Expression of the QCR8 Gene, Which Encodes Subunit VIII of the Mitochondrial Ubiquinol–Cytochrome c Oxidoreductase," *Molecular and Cellular Biology* (1992) 12(6):2872–83.

Gietz, R. D., et al., "New Yeast–*Escherichia Coli* Shuttle Vectors Constructed with In Vitro Mutagenized Yeast Genes Lacking Six–Base Pair Restriction Sites," *Gene* (1988) 74:527–34.
Gottlin–Ninfa, E., et al., "Isolation and Functional Analysis of Sporulation–Induced Transcribed Sequences from Saccharomyces Cerevisiae," *Molecular and Cellular Biology*, (1986) 6(6):2185–97.
Guarente, L., et al., "Distinctly Regulated Tandem Upstream Activation Sites Mediate Catabolite Repression of the CYCI Gene of S. Cerevisiae," *Cell*, (1984) 36:503–11.
Hoffman, C. S., et al., "A Ten–Minute Preparation From Yeast Efficiently Releases Autonomous Plasmids for Transformation of *Escherichia Coli*," *Gene*, (1987) 57:267–72.
Hurt, E. C., et al., "The First Twelve Amino Acids of a Yeast Mitochondrial Outer Membrane Protein Can Direct a Nuclear–Encoded Cytochrome Oxidase Subunit to the Mitochondrial Inner Membrane," *Embo J.*, (1985) 4(13A):3509–18.
Ito, H., et al., "Transformation of Intact Yeast Cells Treated with AlkaliCations," *J. Bacteriology*, (1983) 153(1):163–8.
Johnston, M., et al., "Regulation of Carbon Phosphate Utilization," *The Molecular and Cellular Biology of the Yeast Saccharomyces*, (1992) 220–237.
Klein, C. J. L., "Alleviation of Glucose Repression of Maltose Metabolism by MIGI Disruption in Saccharomyces Cerevisiae," *Applied and Environmental Microbiology*, (1996) 62(12):4441–9.
Lesage, P., et al., "Yeast SNFI Protein Kinase Interacts with SIP4, a $C_6$Zinc Cluster Transcriptional Activator: a New Role for SNFI in the Glucose Response," *Molecular and Cellular Biology* (1996) 16(5):1921–8.
Li, X., et al., "Evolutionary Variation of the CCAAT–Binding Transcription Factor NF–Y," *Nucleic Acids Research*, (1992) 20(5);1087–91.
McKnight, G. L., et al., Selection of Functional cDNAs by Complementation in Yeast, *Proc. Natl. Acad. Sci. USA*, (1983) 80:4412–6.

(List continued on next page.)

*Primary Examiner*—Remy Yucel
(74) *Attorney, Agent, or Firm*—Morrison & Foerster LLP

(57) ABSTRACT

The invention provides methods for changing the metabolic pathways of micro-organisms in the presence of a certain carbon source and uses of such changes, as well as micro-organisms and uses of such changes, as well as micro-organisms produced by these methods. In a preferred embodiment the invention provides new yeast strains with improved biomass yields, a process to obtain these yeasts and the potential application of these yeasts are provided. The biomass yield is improved by the introduction into a yeast of a DNA construct conferring altered expression of a gene encoding a protein controlling transcription of a number of glucose-repressed genes. The yeasts are less sensitive to glucose repression, resulting in an increase in respiratory capacity, reduction of ethanol production and increased conversion of sugar into biomass.

20 Claims, 30 Drawing Sheets

OTHER PUBLICATIONS

Mumberg, D., et al., "Yeast Vectors for the Controlled Expression of Heterologous Proteins in Different Genetic Backgrounds," *Gene*, (1995) 156:119–22.

Needleman, R. B., et al., "MAL6 of Saccharomyces: A Complex Genetic Locus Containing Three Genes Required for Maltose Fermentation," *Proc. Natl. Acad. Sci. USA*, (1984) 81:2811–5.

Nehlin, J. O., et al., "Yeast MIGI Repressor is Related to the Mammalian Early Growth Response and Wilms Tumour Finger Proteins," *Embo J.*, (1990) 9(9):2891–8.

Ng, R., et al., "Isolation and Sequence of the Gene for Actin in Saccharomyces Cerevisiae," *Proc. Natl. Acad. Sci. USA*, (1980) 77(7):3912–6.

Olesen, J., et al., "Yeast HAP2 and HAP3 Activators Both Bind to the CYC1 Upstream Activation Site, UAS2, in an Interdependent Manner," *Cell* (1987) 51:953–61.

Oudshoorn, P., et al., "Subunit II of Yeast $QH_2$ :Cytochrome–c Oxidoreductase: Nucleotide Sequence of the Gene and Features of the Protein," *Eur. J. Biochem.*, (1987) 163:97–103.

Ronne, H., "Glucose Repression In Fungi," Trends In Genet. (1995) 11(1);12–17.

Rothstein, R. J., "One–Step Gene Disruption in Yeast," *Methods in Enzymology*, (1983) 101:202–11.

Sambrook, J., et al., "Analysis and Cloning of Eukaryotic Genomci DNA," *Molecular Cloning: A Laboratory Manual. Second Addition*, (1989) 9.49–9.52.

Sierkstra, L., et al., "Regulation of Glycolytic Enzymes and the Crabtree Effect in Galactose–Limited Continuous Cultures of Saccharomyces Cerevisiae," *Yeast* (1993) 9:787–95.

Sinha, S., et al., "Recombinant Rat CBF–C, the Third Subunit of CBF/NFY, Allows Formation of a Protein–DNA Complex with CBF–A and CBF–B and with Yeast HAP2 and HAP3," *Proc. Natl. Acad. Sci. USA*, (1995) 92:1624–8.

Thevelein, J. M., et al., "Trehalose Synthase: Guard to the Gate of Glycolysis in Yeast," *TIBS* (1995) 20:3–10.

Treitel, M. A., et al., "Repression by SSN6–TUPI is Directed by MIGI, a Repressor/Activator Protein," *Proc. Nat. Acad. Sci. USA*, (1995) 92:3132–6.

Trumbly, R. J., "Glucose Repression in the Yeast Saccharomyces Cerevisiae," *Molecular Microbiology*, (1992) 6(1):15–21.

Van Loon, A. P. G. M., et al., "Transport of Proteins to the Mitochondrial Intermembrane Space: The 'Matrix–Targeting' and the 'Sorting' Domains in the Cytochrome $c_1$ Presequence," *Embo J.*, (1987) 6(8):2433–9.

Van Steeg, H., et al., "Targeting Efficeincy of a Mitochondrial Pre–Sequence is Dependent on the Passenger Protein," *Embo J.*, (1986) 5(13):3643–50.

Wenzel, T. J., et al., "Promoter Analysis of the PDAI Gene Encoding the EI α Subunit of the Pyruvate Dehydrogenase Comples from Saccharomyces Cerevisiae," *Yeast* (1994) 10:297–308.

* cited by examiner

Figure 4: Nucleotide and amino acid sequence of HAP2

```
TCGTTATTTAGCAATCTTACCCGGAAAACTTCTTGTATCGTAACATTAATTCTCCCTTAC
         10        20        30        40        50        60

AAGGGGACCTCGATGAATAAATAAAGTGTTTGTGTTGAAGGTACTTGCAAAAGGGCAACT
         70        80        90       100       110       120

CACTGTCGTTTATAATTTGATTTACTAATCGCATCTGTATTTGGAAAAGCATTTCTTTTT
        130       140       150       160       170       180

M   S   A   D   E   T   D   A   K   F   H   P   L
GGAAGAGGAACAAGAACGCCATGTCAGCAGACGAAACGGATGCGAAATTTCATCCATTAG
        190       200       210       220       230       240

E   T   D   L   Q   S   D   T   A   A   A   T   S   T   A   A   A   S   R   S
AAACAGATCTGCAATCTGATACAGCGGCTGCAACATCAACGGCAGCAGCTTCACGCAGTC
        250       260       270       280       290       300

P   S   L   Q   E   K   P   I   E   M   P   L   D   M   G   K   A   P   S   P
CCTCTCTTCAAGAGAAGCCCATAGAGATGCCCTTGGATATGGGAAAAGCGCCTTCTCCAA
        310       320       330       340       350       360

R   G   E   D   Q   R   V   T   N   E   E   D   L   F   L   F   N   R   L   R
GAGGCGAAGATCAACGGGTTACAAATGAAGAAGATTTGTTTTTGTTTAACAGATTGCGGG
        370       380       390       400       410       420

A   S   Q   N   R   V   M   D   S   L   E   P   Q   Q   Q   S   Q   Y   T   S
CATCACAGAATAGAGTTATGGACTCCTTGGAACCACAACAACAGTCACAGTATACATCTT
        430       440       450       460       470       480

S   S   V   S   T   M   E   P   S   A   D   F   T   S   F   S   A   V   T   T
CCAGTGTCAGTACGATGGAACCATCTGCCGACTTTACTAGTTTCTCTGCAGTGACTACTT
        490       500       510       520       530       540

L   P   P   P   P   H   Q   Q   Q   Q   Q   Q   Q   Q   Q   Q   Q   Q   Q   Q
TACCGCCTCCTCCTCATCAACAACAACAGCAACAACAGCAGCAGCAGCAGCAGCAGCAAT
        550       560       570       580       590       600

L   V   V   Q   A   Q   Y   T   Q   N   Q   P   N   L   Q   S   D   V   L   G
TGGTGGTTCAAGCCCAGTACACCCAAAATCAACCAAACTTGCAAAGCGATGTTTTAGGAA
        610       620       630       640       650       660

-----------------------------------------
  T   A   I   A   E   Q   P   F   Y   V   N   A   K   Q   Y   Y   R   I   L   K
CCGCTATAGCAGAGCAACCATTTTATGTTAATGCCAAGCAGTACTACCGAATTTTGAAAA
        670       680       690       700       710       720

------------------------------
  R   R   Y   A   R   A   K   L   E   E   K   L   R   I   S   R   E   R   K   P
GGCGATATGCAAGAGCTAAACTAGAGGAAAAAGCTACGAATATCAAGAGAACGAAAGCCAT
        730       740       750       760       770       780

Y   L   H   E   S   R   H   K   H   A   M   R   R   P   R   G   E   G   G   R
ACTTACACGAATCTCGACATAAACATGCGATGCGAAGACCTCGTGGTGAAGGTGGGAGGT
        790       800       810       820       830       840

-----------------
  F   L   T   A   A   E   I   K   A   M   K   S   K   K   S   G   A   S   D   D
TCTTGACAGCCGCTGAGATCAAAGCCATGAAATCGAAGAAAAGTGGGGCTAGCGATGATC
        850       860       870       880       890       900
```

Figure 4

```
      P   D   D   S   H   E   D   K   K   I   T   T   K   I   I   Q   E   Q   P   H
CTGACGATAGTCATGAGGATAAAAAAATCACTACTAAAATAATACAAGAACAGCCGCATG
        910         920        930         940         950         960

A   T   S   T   A   A   A   A   D   K   K   T   *
CTACTTCCACCGCAGCTGCAGCAGACAAAAAAACATAATTTTGTAATATTCCAATGTTAA
        970         980         990        1000        1010        1020

TATCATTCCTAAAAGAACTAAAAGTGCCCTCTTATACCACATGGTATCCATATGGCCTAT
       1030        1040        1050        1060        1070        1080

TTAATCTGAATCAATATGTATATGTACTTTTACCAATCTCGTTTCGTTTCGTTTCGTTTC
       1090        1100        1110        1120        1130        1140

ATTTCTAACAGACCTATGTACTCCGCTGGAAAAGAAACCATATTGCGATCGTATTTAC
       1150        1160        1170        1180        1190
```

Figure 5: Nucleotide and amino acid sequence of HAP3

```
CAAACCTTCTGCCAAAATATAGCACAATAGAAGTACCATATTACGTTCGATGCCACGACA
         10        20        30        40        50        60

ATATCGCGCTACGTGCGTTTTTTGGTCCGCTCTTTCAGACTAAGTAAAAAAAGAGCTGCG
         70        80        90       100       110       120

AATAGTAGCTTTCCGCCAATCAAACTCAAGAGCAGGACTAAGCTAGATAGTAACACAAGT
        130       140       150       160       170       180

M  N  T  N  E  S  H  V  S  T  S  P
GGCACAAACCTCTCGAGAATATGAATACCAACGAGTCCGAACATGTTAGCACAAGCCCAG
        190       200       210       220       230       240

E  D  T  Q  E  N  G  G  N  A  S  S  S  G  S  L  Q  Q  I  S
AGGATACTCAGGAGAACGGTGGAAACGCTAGCTCCAGCGGCAGTTTGCAGCAAATTTCCA
        250       260       270       280       290       300

T  L  R  E  Q  D  R  W  L  P  I  N  N  V  A  R  L  M  K  N
CGCTAAGAGAGCAGGACAGATGGCTACCCATCAACAATGTAGCGCGACTCATGAAGAATA
        310       320       330       340       350       360

T  L  P  P  S  A  K  V  S  K  D  A  K  E  C  M  Q  E  C  V
CTCTCCCACCGAGTGCTAAGGTATCGAAAGATGCGAAAGAGTGCATGCAGGAGTGTGTCA
        370       380       390       400       410       420

S  E  L  I  S  F  V  T  S  E  A  S  D  R  C  A  A  D  K  R
GTGAGCTCATTTCTTTTGTGACTAGCGAGGCCAGCGATCGATGCGCTGCTGACAAAAGAA
        430       440       450       460       470       480

K  T  I  N  G  E  D  I  L  I  S  L  H  A  L  G  F  E  N  Y
AGACGATAAACGGGGAAGACATTCTCATATCATTGCACGCCTTAGGATTCGAGAACTATG
        490       500       510       520       530       540

A  E  V  L  K  I  Y  L  A  K  Y  R  Q  Q  Q  A  L  K  N  Q
CAGAGGTGTTGAAAATCTACTTGGCTAAATACAGGCAACAACAGGCGCTGAAGAATCAAC
        550       560       570       580       590       600

L  M  Y  E  Q  D  D  E  E  V  P  *
TAATGTATGAGCAGGACGACGAAGAGGTGCCTTGAGAAGACAAAACCAGGTGGTAGATCG
        610       620       630       640       650       660

CAAAAGTTGCTAGCTGTCAGGATGGAATAGCACGGGGCTATTTCCTGCTGGTCGTTGGTT
        670       680       690       700       710       720

CTCGTGTAATTAATGAATGTAACGATATAGATAATATTTTATTGTTAGTGTGTAATGTAT
        730       740       750       760       770       780

TCAATGTAATGTATGGGTGCTTTGTAAAGGGTGTATGATGTTTGCCACCGGAAGG
        790       800       810       820       830
```

Figure 5

Figure 6: Nucleotide and amino acid sequence of HAP4

```
TAAAGGAACCAGAAAAATAAAAAAGGGTCATTATTTATTTGAGCAGATCATTATCAAACG
        10        20        30        40        50        60
CATAGGAAGAGAAAAAACACAGTTTTATTTTTTTTCCACACATATTTATTGGTCTCCTAG
        70        80        90       100       110       120
TACATCAAAGAGCATTTTAATGGGTTGCTGATTTGTTTTACCTACATTTTCTAGTACAAA
       130       140       150       160       170       180
                            M  T  A  K  T  F  L  L  Q  A  S  A  S
AAAAAAACAAAAAAAGAATCATGACCGCAAAGACTTTTCTACTACAGGCCTCCGCTAGTC
       190       200       210       220       230       240
 R  P  R  S  N  H  F  K  N  E  H  N  N  I  P  L  A  P  V  P
GCCCTCGTAGTAACCATTTTAAAAATGAGCATAATAATATTCCATTGGCGCCTGTACCGA
       250       260       270       280       290       300
 I  A  P  N  T  N  H  H  N  N  S  S  L  E  F  E  N  D  G  S
TCGCCCCAAATACCAACCATCATAACAATAGTTCGCTGGAATTCGAAAACGATGGCAGTA
       310       320       330       340       350       360
 K  K  K  K  S  S  L  V  V  R  T  S  K  H  W  V  L  P  P
AAAAGAAGAAGAAGTCTAGCTTGGTGGTTAGAACTTCAAAACATTGGGTTTTGCCCCCAA
       370       380       390       400       410       420
 R  P  R  P  G  R  R  S  S  S  H  N  T  L  P  A  N  N  T  N
GACCAAGACCTGGTAGAAGATCATCTTCTCACAACACTCTACCTGCCAACAACACCAATA
       430       440       450       460       470       480
 N  I  L  N  V  G  P  N  S  R  N  S  S  N  N  N  N  N  N
ATATTTTAAATGTTGGCCCTAACAGCAGGAACAGTAGTAATAATAATAATAATAATAACA
       490       500       510       520       530       540
 I  I  S  N  R  K  Q  A  S  K  E  K  R  K  I  P  P  H  I  Q
TCATTTCGAATAGGAAACAAGCTTCCAAAGAAAAGAGGAAAATACCAAGACATATCCAGA
       550       560       570       580       590       600
 T  I  D  E  K  L  I  N  D  S  N  Y  L  A  F  L  K  F  D  D
CAATCGATGAAAAGCTAATAAACGACTCGAATTACCTCGCATTTTTGAAGTTCGATGACT
       610       620       630       640       650       660
 L  E  N  E  K  F  H  S  S  A  S  S  I  S  S  P  S  Y  S  S
TGGAAAATGAAAAGTTTCATTCTTCTGCCTCCTCCATTTCATCTCCATCTTATTCATCTC
       670       680       690       700       710       720
 P  S  F  S  S  Y  R  N  R  K  K  S  E  F  M  D  D  E  S  C
CATCTTTTTCAAGTTATAGAAATAGAAAAAAAATCAGAATTCATGGACGATGAAAGCTGCA
       730       740       750       760       770       780
 T  D  V  E  T  I  A  A  H  N  S  L  L  T  K  N  H  H  I  D
CCGATGTGGAAACCATTGCTGCTCACAACAGTCTGCTAACAAAAAAACCATCATATAGATT
       790       800       810       820       830       840
 S  S  S  N  V  H  A  P  P  T  K  K  S  K  L  N  D  F  D  L
CTTCTTCAAATGTTCACGCACCACCCACGAAAAAAATCAAAGTTGAACGACTTTGATTTAT
       850       860       870       880       890       900
 L  S  L  S  S  T  S  S  A  T  P  V  P  Q  L  T  K  D  L
TGTCCTTATCTTCCACATCTTCATCGGCCACTCCGGTCCCACAGTTGACAAAAGATTTGA
       910       920       930       940       950       960
```

Figure 6

```
         N  M  N  L  N  F  H  K  I  P  H  K  A  S  F  P  D  S  P  A
        ACATGAACCTAAATTTTCATAAGATCCCTCATAAGGCTTCATTCCCTGATTCTCCAGCAG
           970       980       990      1000      1010      1020

D  F  S  P  A  D  S  V  S  L  I  R  N  H  S  L  P  T  N  L
        ATTTCTCTCCAGCAGATTCAGTCTCGTTGATTAGAAACCACTCCTTGCCTACTAATTTGC
          1030      1040      1050      1060      1070      1080

Q  V  K  D  K  I  E  D  L  N  E  I  K  F  F  N  D  F  E  K
        AAGTTAAGGACAAAATTGAGGATTTGAACGAGATTAAATTCTTTAACGATTTCGAGAAAC
          1090      1100      1110      1120      1130      1140

L  E  F  F  N  K  Y  A  K  V  N  T  N  N  D  V  N  E  N  N
        TTGAGTTTTTCAATAAGTATGCCAAAGTCAACACGAATAACGACGTTAACGAAAATAATG
          1150      1160      1170      1180      1190      1200

D  L  W  N  S  Y  L  Q  S  M  D  D  T  T  G  K  N  S  G  N
        ATCTCTGGAATTCTTACTTACAGTCTATGGACGATACAACAGGTAAGAACAGTGGCAATT
          1210      1220      1230      1240      1250      1260

Y  Q  Q  V  D  N  D  D  N  M  S  L  L  N  L  P  I  L  E  E
        ACCAACAAGTGGACAATGACGATAATATGTCTTTATTGAATCTGCCAATTTTGGAGGAAA
          1270      1280      1290      1300      1310      1320

T  V  S  S  G  Q  D  D  K  V  E  P  D  E  E  D  I  W  N  Y
        CCGTATCTTCAGGGCAAGATGATAAGGTTGAGCCAGATGAAGAAGACATTTGGAATTATT
          1330      1340      1350      1360      1370      1380

L  P  S  S  S  S  Q  Q  E  D  S  S  R  A  L  K  K  N  T  N
        TACCAAGTTCAAGTTCACAACAAGAAGATTCATCACGTGCTTTGAAAAAAAATACTAATT
          1390      1400      1410      1420      1430      1440
                                                  ----------------

S  E  K  A  N  I  Q  A  K  N  D  E  T  Y  L  F  L  Q  D  Q
        CTGAGAAGGCGAACATCCAAGCAAAGAACGATGAAACCTATCTGTTTCTTCAGGATCAGG
          1450      1460      1470      1480      1490      1500
        ------------------------------------------------------------

D  E  S  A  D  S  H  H  H  D  E  L  G  S  E  I  T  L  A  D
        ATGAAAGCGCTGATTCGCATCACCATGACGAGTTAGGTTCAGAAATCACTTTGGCTGACA
          1510      1520      1530      1540      1550      1560
        ---------------------------------------------------------

N  K  F  S  Y  L  P  P  T  L  E  E  L  M  E  E  Q  D  C  N
        ATAAGTTTTCTTATTTGCCCCCAACTCTAGAAGAGTTGATGGAAGAGCAGGACTGTAACA
          1570      1580      1590      1600      1610      1620

N  G  R  S  F  K  N  F  M  F  S  N  D  T  G  I  D  G  S  A
        ATGGCAGATCTTTTAAAAATTTCATGTTTTCCAACGATACCGGTATTGACGGTAGTGCCG
          1630      1640      1650      1660      1670      1680

G  T  D  D  Y  T  K  V  L  K  S  K  K  I  S  T  S  K  S
        GTACTGATGACGACTACACCAAAGTTCTGAAATCCAAAAAAATTTCTACGTCGAAGTCGA
          1690      1700      1710      1720      1730      1740
                      ------------------------------------------

N  A  N  L  Y  D  L  N  D  N  N  D  A  T  A  T  N  E  L
        ACGCTAACCTTTATGACTTAAACGATAACAACAATGATGCAACTGCCACCAATGAACTTG
          1750      1760      1770      1780      1790      1800
        ------------------------------------------------------------

D  Q  S  S  F  I  D  D  L  D  E  D  V  D  F  L  K  V  Q  V
        ATCAAAGCAGTTTCATCGACGACCTTGACGAAGATGTCGATTTTTTAAAGGTACAAGTAT
```

```
         1810       1820       1830      1840      1850      1860
F    *
TTTGAAATAGGCATGTTGCAATAAAACGAAAACAACTAAAAATCACGAAAACAAAATGAT
        1870      1880      1890      1900      1910      1920

ATTATACAATAAAAAATTCTTATTATGGGTAATGATAGTATTCTTCGCCTGCTTAGGCGT
        1930       1940      1950      1960      1970      1980

CCTTTTCCTTCAACAACAAAAATTCCAAAAAAAAAAAGTAAAAAAACAAAACTTTGATTG
        1990      2000      2010      2020      2030      2040

TTTTTTAATGATGTTAATGATTTTT
      2050      2060
```

Figure 8: Nucleotide and amino acid sequence of the ADH1 promoter fused to the coding region of HAP4

```
atccttttgttgtttccgggtgtacaatatggacttcctcttttctggcaaccaaaccca
         10        20        30        40        50
60 tacatcgggattcctataataccttcgttggtctccctaacatgtaggtggcggagggga
         70        80        90       100       110
120 gatatacaatagaacagataccagacaagacataatgggctaaacaagactacaccaatt
        130       140       150       160       170
180 acactgcctcattgatggtggtacataacgaactaatactgtagccctagacttgatagc
        190       200       210       220       230
240 catcatcatatcgaagtttcactaccctttttccatttgccatctattgaagtaataata
        250       260       270       280       290
300 ggcgcatgcaacttcttttcttttttttcttttctctctcccccgttgttgtctcacca
        310       320       330       340       350
360 tatccgcaatgacaaaaaaatgatggaagacactaaaggaaaaaattaacgacaaagac
        370       380       390       400       410
420 agcaccaacagatgtcgttgttccagagctgatgaggggtatcttcgaacacacgaaact
        430       440       450       460       470
480 ttttccttccttcattcacgcacactactctctaatgagcaacggtatacggccttcctt
        490       500       510       520       530
540 ccagttacttgaatttgaaataaaaaaagtttgccgctttgctatcaagtataaatagac
        550       560       570       580       590
600 ctgcaattattaatcttttgtttcctcgtcattgttctcgttcccttcttccttgtttc
```

Figure 8

```
              610       620       630       640       650
     660
     ttttctgcacaatatttcaagctataccaagcatacaatcaaggaattcgagctcgccc
          670       680       690       700       710
     720
          M  T  A  K  T  F  L  L  Q  A  S  A  S  R  P  R  S  N_ H
     F
     cATGACCGCAAAGACTTTTCTACTACAGGCCTCCGCTAGTCGCCCTCGTAGTAACCATTT
          730       740       750       760       770
     780
          K  N  E  H  N  N  I  P  L  A  P  V  P  I  A  P  N  T  N
     H
     TAAAAATGAGCATAATAATATTCCATTGGCGCCTGTACCGATCGCCCCAAATACCAACCA
          790       800       810       820       830
     840
          H  N  N  S  S  L  E  F  E  N  D  G  S  K  K  K  K  S
     S
     TCATAACAATAGTTCGCTGGAATTCGAAAACGATGGCAGTAAAAAGAAGAAGAAGTCTAG
          850       860       870       880       890
     900
          L  V  V  R  T  S  K  H  W  V  L  P  P  R  P  R  P  G  R
     R
     CTTGGTGGTTAGAACTTCAAAACATTGGGTTTTGCCCCAAGACCAAGACCTGGTAGAAG
          910       920       930       940       950
     960
          S  S  S  H  N  T  L  P  A  N  N  T  N  N  I  L  N  V  G
     P
     ATCATCTTCTCACAACACTCTACCTGCCAACAACACCAATAATATTTTAAATGTTGGCCC
          970       980       990       1000      1010
     1020
          N  S  R  N  S  S  N  N  N  N  N  N  I  I  S  N  R  K
     Q
     TAACAGCAGGAACAGTAGTAATAATAATAATAATAATAACATCATTTCGAATAGGAAACA
          1030      1040      1050      1060      1070
     1080
          A  S  K  E  K  R  K  I  P  R  H  I  Q  T  I  D  E  K  L
     I
     AGCTTCCAAAGAAAAGAGGAAAATACCAAGACATATCCAGACAATCGATGAAAAGCTAAT
          1090      1100      1110      1120      1130
     1140
```

```
        N  D  S  N  Y  L  A  F  L  K  F  D  D  L  E  N  E  K  F
R

AAACGACTCGAATTACCTCGCATTTTTGAAGTTCGATGACTTGGAAAATGAAAAGTTTCG
         1150      1160      1170      1180      1190
1200

S  S  A  S  S  I  S  S  P  S  Y  S  S  P  S  F  S  S  Y
R

TTCTTCTGCCTCCTCCATTTCATCTCCATCTTATTCATCTCCATCTTTTTCAAGTTATAG
         1210      1220      1230      1240      1250
1260

N  R  K  K  S  E  F  M  D  D  E  S  C  T  D  V  E  T  I
A

AAATAGAAAAAAATCAGAATTCATGGACGATGAAAGCTGCACCGATGTGGAAACCATTGC
         1270      1280      1290      1300      1310
1320

A  H  N  S  L  L  T  K  N  H  H  I  D  S  S  S  N  V  H
A

TGCTCACAACAGTCTGCTAACAAAAAACCATCATATAGATTCTTCTTCAAATGTTCACGC
         1330      1340      1350      1360      1370
1380

P  P  T  K  K  S  K  L  N  D  F  D  L  L  S  L  S  S  T
S

ACCACCCACGAAAAAATCAAAGTTGAACGACTTTGATTTATTGTCCTTATCTTCCACATC
         1390      1400      1410      1420      1430
1440

S  S  A  T  P  V  P  Q  L  T  K  D  L  N  M  N  L  N  F
H

TTCATCGGCCACTCCGGTCCCACAGTTGACAAAAGATTTGAACATGAACCTAAATTTTCA
         1450      1460      1470      1480      1490
1500

K  I  P  H  K  A  S  F  P  D  S  P  A  D  F  S  P  A  D
S

TAAGATCCCTCATAAGGCTTCATTCCCTGATTCTCCAGCAGATTTCTCTCCAGCAGATTC
         1510      1520      1530      1540      1550
1560

V  S  L  I  R  N  H  S  L  P  T  N  L  Q  V  K  D  K  I
E

AGTCTCGTTGATTAGAAACCACTCCTTGCCTACTAATTTGCAAGTTAAGGACAAAATTGA
         1570      1580      1590      1600      1610
1620

D  L  N  E  I  K  F  F  N  D  F  E  K  L  E  F  F  N  K
Y
```

```
GGATTTGAACGAGATTAAATTCTTTAACGATTTCGAGAAACTTGAGTTTTTCAATAAGTA
         1630      1640      1650      1660      1670
1680

A   K   V   N   T   N   N   D   V   N   E   N   N   D   L   W   N   S   Y
L

TGCCAAAGTCAACACGAATAACGACGTTAACGAAAATAATGATCTCTGGAATTCTTACTT
         1690      1700      1710      1720      1730
1740

Q   S   M   D   D   T   T   G   K   N   S   G   N   Y   Q   Q   V   D   N
D

ACAGTCTATGGACGATACAACAGGTAAGAACAGTGGCAATTACCAACAAGTGGACAATGA
         1750      1760      1770      1780      1790
1800

D   N   M   S   L   L   N   L   P   I   L   E   E   T   V   S   S   G   Q
D

CGATAATATGTCTTTATTGAATCTGCCAATTTTGGAGGAAACCGTATCTTCAGGGCAAGA
         1810      1820      1830      1840      1850
1860

D   K   V   E   P   D   E   E   D   I   W   N   Y   L   P   S   S   S   S
Q

TGATAAGGTTGAGCCAGATGAAGAAGACATTTGGAATTATTTACCAAGTTCAAGTTCACA
         1870      1880      1890      1900      1910
1920

Q   E   D   S   S   R   A   L   K   K   N   T   N   S   E   K   A   N   I
Q

ACAAGAAGATTCATCACGTGCTTTGAAAAAAAATACTAATTCTGAGAAGGCGAACATCCA
          1930      1940      1950      1960      1970
1980

A   K   N   D   E   T   Y   L   F   L   Q   D   Q   D   E   S   A   D   S
H

AGCAAAGAACGATGAAACCTATCTGTTTCTTCAGGATCAGGATGAAAGCGCTGATTCGCA
          1990      2000      2010      2020      2030
2040

H   H   D   E   L   G   S   E   I   T   L   A   D   N   K   F   S   Y   L
P

TCACCATGACGAGTTAGGTTCAGAAATCACTTTGGCTGACAATAAGTTTTCTTATTTGCC
         2050      2060      2070      2080      2090
2100

P   T   L   E   E   L   M   E   E   Q   D   C   N   N   G   R   S   F   K
N

CCCAACTCTAGAAGAGTTGATGGAAGAGCAGGACTGTAACAATGGCAGATCTTTTAAAAA
```

```
              2110        2120        2130        2140        2150
    2160
         F   M   F   S   N   D   T   G   I   D   G   S   A   G   T   D   D   D   Y
    T
TTTCATGTTTTCCAACGATACCGGTATTGACGGTAGTGCCGGTACTGATGACGACTACAC
            2170        2180        2190        2200        2210
    2220

K   V   L   K   S   K   K   I   S   T   S   K   S   N   A   N   L   Y   D
    L
CAAAGTTCTGAAATCCAAAAAAATTTCTACGTCGAAGTCGAACGCTAACCTTTATGACTT
            2230        2240        2250        2260        2270
    2280

N   D   N   N   D   A   T   A   T   N   E   L   D   Q   S   F   I
    D
AAACGATAACAACAATGATGCAACTGCCACCAATGAACTTGATCAAAGCAGTTTCATCGA
            2290        2300        2310        2320        2330
    2340

D   L   D   E   D   V   D   F   L   K   V   Q   V   *
    CGACCTTGACGAAGATGTCGATTTTTTAAAGGTACAAGTATTTTAAggggatcc
            2350        2360        2370        2380        2390
```

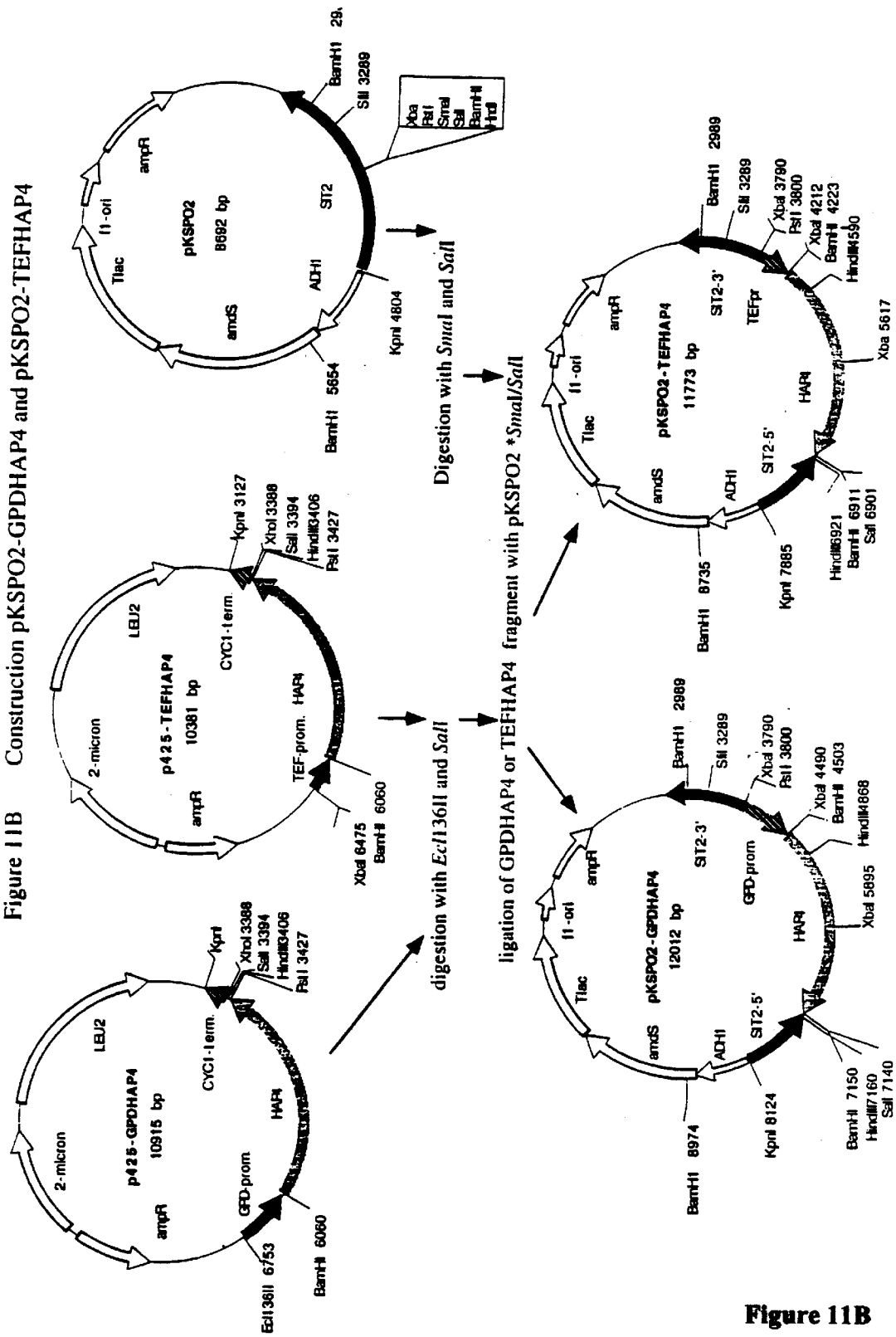
Figure 11B Construction pKSPO2-GPDHAP4 and pKSPO2-TEFHAP4

Figure 12A.   Nucleotide and amino acid sequence of the 680 bp
              GPD1 promoter fused to the HAP4 coding region,
              as cloned in pKSPO2 and integrated in the yeast
              genome

```
1                               31
gag ctc tgg ggt ttg agc aag tct aag ttt acg tag cat aaa aat tct cgg att gcg tca 61                              91
aat aat aaa aaa agt aac ccc act tct act tct aca tcg gaa aaa cat tcc att cac ata 121                             151
tcg tct ttg gcc tat ctt gtt ttg tcc tcg gta gat cag gtc agt aca aac gca aca cga 181                             211
aag aac aaa aaa aga aga aaa cag aag gcc aag aca ggg tca atg aga ctg ttg tcc tcc 241                             271
tac tgt ccc tat gtc tct ggc cga tca cgc gcc att gtc cct cag aaa caa atc aaa cac 301                             331
cca cac ccc ggg cac cca aag tcc cca ccc aca cca cca ata cgt aaa cgg ggc gcc ccc 361                             391
tgc agg ccc tcc tgc gcg cgg cct ccc gcc ttg ctt ctc tcc cct tcc ttt tct ttt tcc 421                             451
agt ttt ccc tat ttt gtc cct ttt tcc gca caa caa gta tca gaa tgg gtt cat caa atc 481                             511
tat cca acc taa ttc gca cgt aga ctg gct tgg tat tgg cag ttt cgt agt tat ata tat 541                             571
act acc atg agt gaa act gtt acg tta cct taa att ctt tct ccc ttt aat ttt ctt tta 601                             631
tct tac tct cct aca taa gac atc aag aaa caa ttg tat att gta cac ccc ccc cct cca 661                             691
caa aca caa ata ttg ata ata taa agt cta gaa cta gtg gat ccc ccc ATG ACC GCA AAG
                                                                 M   T   A   K
721                             751
ACT TTT CTA CTA CAG GCC TCC GCT AGT CGC CCT CGT AGT AAC CAT TTT AAA AAT GAG CAT
 T   F   L   L   Q   A   S   A   S   R   P   R   S   N   H   F   K   N   E   H
781                             811
AAT AAT ATT CCA TTG GCG CCT GTA CCG ATC GCC CCA AAT ACC AAC CAT CAT AAC AAT AGT
 N   N   I   P   L   A   P   V   P   I   A   P   N   T   N   H   H   N   N   S
841                             871
TCG CTG GAA TTC GAA AAC GAT GGC AGT AAA AAG AAG AAG AAG TCT AGC TTG GTG GTT AGA
 S   L   E   F   E   N   D   G   S   K   K   K   K   K   S   S   L   V   V   R
901                             931
ACT TCA AAA CAT TGG GTT TTG CCC CCA AGA CCA AGA CCT GGT AGA AGA TCA TCT TCT CAC
 T   S   K   H   W   V   L   P   P   R   P   R   P   G   R   R   S   S   S   H
961                             991
AAC ACT CTA CCT GCC AAC AAC ACC AAT AAT ATT TTA AAT GTT GGC CCT AAC AGC AGG AAC
 N   T   L   P   A   N   N   T   N   N   I   L   N   V   G   P   N   S   R   N
1021                            1051
AGT AGT AAT AAT AAT AAT AAT AAT AAC ATC ATT TCG AAT AGG AAA CAA GCT TCC AAA GAA
```

Figure 12A

```
    S   S   N   N   N   N   N   N   I   I   S   N   R   K   Q   A   S   K   E
1081                                        1111
AAG AGG AAA ATA CCA AGA CAT ATC CAG ACA ATC GAT GAA AAG CTA ATA AAC GAC TCG AAT
 K   R   K   I   P   R   H   I   Q   T   I   D   E   K   L   I   N   D   S   N
1141                                        1171
TAC CTC GCA TTT TTG AAG TTC GAT GAC TTG GAA AAT GAA AAG TTT CAT TCT TCT GCC TCC
 Y   L   A   F   L   K   F   D   D   L   E   N   E   K   F   H   S   S   A   S
1201                                        1231
TCC ATT TCA TCT CCA TCT TAT TCA TCT CCA TCT TTT TCA AGT TAT AGA AAT AGA AAA AAA
 S   I   S   S   P   S   Y   S   S   P   S   F   S   S   Y   R   N   R   K   K
1261                                        1291
TCA GAA TTC ATG GAC GAT GAA AGC TGC ACC GAT GTG GAA ACC ATT GCT GCT CAC AAC AGT
 S   E   F   M   D   D   E   S   C   T   D   V   E   T   I   A   A   H   N   S
1321                                        1351
CTG CTA ACA AAA AAC CAT CAT ATA GAT TCT TCT TCA AAT GTT CAC GCA CCA CCC ACG AAA
 L   L   T   K   N   H   H   I   D   S   S   S   N   V   H   A   P   P   T   K
1381                                        1411
AAA TCA AAG TTG AAC GAC TTT GAT TTA TTG TCC TTA TCT TCC ACA TCT TCA TCG GCC ACT
 K   S   K   L   N   D   F   D   L   L   S   L   S   S   T   S   S   S   A   T
1441                                        1471
CCG GTC CCA CAG TTG ACA AAA GAT TTG AAC ATG AAC CTA AAT TTT CAT AAG ATC CCT CAT
 P   V   P   Q   L   T   K   D   L   N   M   N   L   N   F   H   K   I   P   H
1501                                        1531
AAG GCT TCA TTC CCT GAT TCT CCA GCA GAT TTC TCT CCA GCA GAT TCA GTC TCG TTG ATT
 K   A   S   F   P   D   S   P   A   D   F   S   P   A   D   S   V   S   L   I
1561                                        1591
AGA AAC CAC TCC TTG CCT ACT AAT TTG CAA GTT AAG GAC AAA ATT GAG GAT TTG AAC GAG
 R   N   H   S   L   P   T   N   L   Q   V   K   D   K   I   E   D   L   N   E
1621                                        1651
ATT AAA TTC TTT AAC GAT TTC GAG AAA CTT GAG TTT TTC AAT AAG TAT GCC AAA GTC AAC
 I   K   F   F   N   D   F   E   K   L   E   F   F   N   K   Y   A   K   V   N
1681                                        1711
ACG AAT AAC GAC GTT AAC GAA AAT AAT GAT CTC TGG AAT TCT TAC TTA CAG TCT ATG GAC
 T   N   N   D   V   N   E   N   N   D   L   W   N   S   Y   L   Q   S   M   D
1741                                        1771
GAT ACA ACA GGT AAG AAC AGT GGC AAT TAC CAA CAA GTG GAC AAT GAC GAT AAT ATG TCT
 D   T   T   G   K   N   S   G   N   Y   Q   Q   V   D   N   D   D   N   M   S
1801                                        1831
TTA TTG AAT CTG CCA ATT TTG GAG GAA ACC GTA TCT TCA GGG CAA GAT GAT AAG GTT GAG
 L   L   N   L   P   I   L   E   E   T   V   S   S   G   Q   D   D   K   V   E
1861                                        1891
CCA GAT GAA GAA GAC ATT TGG AAT TAT TTA CCA AGT TCA AGT TCA CAA CAA GAA GAT TCA
 P   D   E   E   D   I   W   N   Y   L   P   S   S   S   Q   Q   E   D   S
1921                                        1951
TCA CGT GCT TTG AAA AAA AAT ACT AAT TCT GAG AAG GCG AAC ATC CAA GCA AAG AAC GAT
 S   R   A   L   K   K   N   T   N   S   E   K   A   N   I   Q   A   K   N   D
1981                                        2011
GAA ACC TAT CTG TTT CTT CAG GAT CAG GAT GAA AGC GCT GAT TCG CAT CAC CAT GAC GAG
 E   T   Y   L   F   L   Q   D   Q   D   E   S   A   D   S   H   H   H   D   E
2041                                        2071
TTA GGT TCA GAA ATC ACT TTG GCT GAC AAT AAG TTT TCT TAT TTG CCC CCA ACT CTA GAA
 L   G   S   E   I   T   L   A   D   N   K   F   S   Y   L   P   P   T   L   E
2101                                        2131
GAG TTG ATG GAA GAG CAG GAC TGT AAC AAT GGC AGA TCT TTT AAA AAT TTC ATG TTT TCC
 E   L   M   E   E   Q   D   C   N   N   G   R   S   F   K   N   F   M   F   S
2161                                        2191
AAC GAT ACC GGT ATT GAC GGT AGT GCC GGT ACT GAT GAC GAC TAC ACC AAA GTT CTG AAA
 N   D   T   G   I   D   G   S   A   G   T   D   D   D   Y   T   K   V   L   K
2221                                        2251
```

```
TCC AAA AAA ATT TCT ACG TCG AAG TCG AAC GCT AAC CTT TAT GAC TTA AAC GAT AAC AAC
 S   K   K   I   S   T   S   K   S   N   A   N   L   Y   D   L   N   D   N   N
2281                                        2311
AAT GAT GCA ACT GCC ACC AAT GAA CTT GAT CAA AGC AGT TTC ATC GAC GAC CTT GAC GAA
 N-  D   A   T   A   T   N   E   L   D   Q   S   S   F   I   D   D   L   D   E
2341                                        2371
GAT GTC GAT TTT TTA Aag gta caa gta ttt tga aat agg cat gtt gca ata aaa cga aaa
 D   V   D   F   L   K   V   Q   V   F   *
2401                                        2431
caa cta aaa atc acg aaa aca aaa tga tat tat aca ata aaa aat tct tat tat ggg taa 2461                                        2491
tga tag tat tct tcg cct gct tag gcg tcc ttt tcc ttc aac aac aaa aat tcc aaa aaa 2521                                        2551
aaa aag taa aaa aac aaa act ttg att gtt ttt taa tga tgt taa tga ttt ttt ttt tct 2581                                        261
ttc ttt atc ata aaa aaa aag tta aaa tga aaa aca aat atg ggt ctg gaa ggc cat tat 2641                                        2671
ttt ttt ttt att tat ata ccg ttt ctg gta ctt agt tat tta ttc tca tac ata cac tat 2701                                        2731
att caa att acc taa gag cat ttt cac ata tcc gtt tac ttt cat ttt ttt ttt ttt tgc 2761                                        2791
ttc ctt ttt aca tat ctt ccg tat atc aca tca cgt tta cgc gta tgg tga aac acg tca 2821                                        2851
aga gaa aaa tga taa aat caa att ttg att tac atc agg ctc cac agg aca ggg aaa tct 2881                                        2911
atc tag tga ggc gat aac tgt agt tcg atg tac tca ttt gaa ctg gac aaa ttg aaa att 2941                                        2971
gag ctg aaa aca tgg gag cat gat ttc att gat aaa aat aaa agg gaa ccc aca agg gat 3001                                        3031
gac acc aag agc ctg cgg act gtt cgg cag atg tat aaa caa tat tcc aca ctg aag aag 3061                                        3091
aaa caa tct ttg caa cga caa aaa gtt gac act caa gag tcg gtt gaa ctc ccg gca cat 3121                                        3151
aaa aaa gac cac gac gaa gtc gta gag ata ggc cct act ccc caa gtt tac ggt aag gcg 3181                                        3211
att agt atc ttt gac atg aat ttg tcg cct ata aag cct ata tac atg aca ttc aca aat 3241                                        3271
aat att gat gtt aac aat gat aac tcc aag aca att tct aat gaa tct tct cca cga aaa 3301                                        3331
act att ctc cta aaa tcg tcg cct gca gga att cga tat caa gct tat cga tac cgt cga
```

Figure 12B. Nucleotide and amino acid sequence of the 402 bp TEF2 promoter fused to the HAP4 coding region, as cloned in pKSP02 and integrated in the yeast genome

```
2                                         32
agc tca atg ttt cta ctc ctt ttt tac tct tcc aga ttt tct cgg act ccg cgc atc gcc 62                                        92
gta cca ctt caa aac acc caa gca cag cat act aaa ttt ccc ctc ttt ctt cct cta ggg 122                                       152
tgt cgt taa tta ccc gta cta aag gtt tgg aaa aga aaa aag aga ccg cct cgt ttc ttt 182                                       212
ttc ttc gtc gaa aaa ggc aat aaa aat ttt tat cac gtt tct ttt tct tga aaa ttt ttt 242                                       272
ttt ttg att ttt ttc tct ttc gat gac ctc cca ttg ata ttt aag tta ata aac ggt ctt 302                                       332
caa ttt ctc aag ttt cag ttt cat ttt tct tgt tct att aca act ttt ttt act tct tgc 362                                       392
tca tta gaa aga aag cat agc aat cta atc taa gtt tta att aca aat cta gaa cta gtg 422                                       452
gat ccc ccc ATG ACC GCA AAG ACT TTT CTA CTA CAG GCC TCC GCT AGT CGC CCT CGT AGT
            M   T   A   K   T   F   L   L   Q   A   S   A   S   R   P   R   S
482                                       512
AAC CAT TTT AAA AAT GAG CAT AAT AAT ATT CCA TTG GCG CCT GTA CCG ATC GCC CCA AAT
N   H   F   K   N   E   H   N   N   I   P   L   A   P   V   P   I   A   P   N
542                                       572
ACC AAC CAT CAT AAC AAT AGT TCG CTG GAA TTC GAA AAC CAT GGC AGT AAA AAG AAG AAG
T   N   H   H   N   N   S   S   L   E   F   E   N   D   G   S   K   K   K   K
602                                       632
AAG TCT AGC TTG GTG GTT AGA ACT TCA AAA CAT TGG GTT TTG CCC CCA AGA CCA AGA CCT
K   S   S   L   V   V   R   T   S   K   H   W   V   L   P   P   R   P   R   P
662                                       692
GGT AGA AGA TCA TCT TCT CAC AAC ACT CTA CCT GCC AAC AAC ACC AAT AAT ATT TTA AAT
G   R   R   S   S   S   H   N   T   L   P   A   N   N   T   N   N   I   L   N
722                                       752
GTT GGC CCT AAC AGC AGG AAC AGT AGT AAT AAT AAT AAT AAT AAC ATC ATT TCG AAT
V   G   P   N   S   R   N   S   S   N   N   N   N   N   N   I   I   S   N
782                                       812
AGG AAA CAA GCT TCC AAA GAA AAG AGG AAA ATA CCA AGA CAT ATC CAG ACA ATC GAT GAA
R   K   Q   A   S   K   E   K   R   K   I   P   R   H   I   Q   T   I   D   E
842                                       872
AAG CTA ATA AAC GAC TCG AAT TAC CTC GCA TTT TTG AAG TTC GAT GAC TTG GAA AAT GAA
K   L   I   N   D   S   N   Y   L   A   F   L   K   F   D   D   L   E   N   E
902                                       932
AAG TTT CAT TCT TCT GCC TCC TCC ATT TCA TCT CCA TCT TAT TCA TCT CCA TCT TTT TCA
K   F   H   S   S   A   S   S   I   S   S   P   Y   S   S   P   S   F   S
962                                       992
AGT TAT AGA AAT AGA AAA AAA TCA GAA TTC ATG GAC GAT GAA AGC TGC ACC GAT GTG GAA
S   Y   R   N   R   K   K   S   E   F   M   D   D   E   S   C   T   D   V   E
```

```
1022                                            1052
ACC ATT GCT GCT CAC AAC AGT CTG CTA ACA AAA AAC CAT CAT ATA GAT TCT TCT TCA AAT
 T   I   A   A   H   N   S   L   L   T   K   N   H   H   I   D   S   S   S   N
1082                                            1112
GTT CAC GCA CCA CCC ACG AAA AAA TCA AAG TTG AAC GAC TTT GAT TTA TTG TCC TTA TCT
 V   H   A   P   P   T   K   K   S   K   L   N   D   F   D   L   L   S   L   S
1142                                            1172
TCC ACA TCT TCA TCG GCC ACT CCG GTC CCA CAG TTG ACA AAA GAT TTG AAC ATG AAC CTA
 S   T   S   S   S   A   T   P   V   P   Q   L   T   K   D   L   N   M   N   L
1202/401                                        1232
AAT TTT CAT AAG ATC CCT CAT AAG GCT TCA TTC CCT GAT TCT CCA GCA GAT TTC TCT CCA
 N   F   H   K   I   P   H   K   A   S   F   P   D   S   P   A   D   F   S   P
1262                                            1292
GCA GAT TCA GTC TCG TTG ATT AGA AAC CAC TCC TTG CCT ACT AAT TTG CAA GTT AAG GAC
 A   D   S   V   S   L   I   R   N   H   S   L   P   T   N   L   Q   V   K   D
1322                                            1352
AAA ATT GAG GAT TTG AAC GAG ATT AAA TTC TTT AAC GAT TTC GAG AAA CTT GAG TTT TTC
 K   I   E   D   L   N   E   I   K   F   F   N   D   F   E   K   L   E   F   F
1382                                            1412
AAT AAG TAT GCC AAA GTC AAC ACG AAT AAC GAC GTT AAC GAA AAT AAT GAT CTC TGG AAT
 N   K   Y   A   K   V   N   T   N   N   D   V   N   E   N   N   D   L   W   N
1442                                            1472
TCT TAC TTA CAG TCT ATG GAC GAT ACA ACA GGT AAG AAC AGT GGC AAT TAC CAA CAA GTG
 S   Y   L   Q   S   M   D   D   T   T   G   K   N   S   G   N   Y   Q   Q   V
1502                                            1532
GAC AAT GAC GAT AAT ATG TCT TTA TTG AAT CTG CCA ATT TTG GAG GAA ACC GTA TCT TCA
 D   N   D   D   N   M   S   L   L   N   L   P   I   L   E   E   T   V   S   S
1562                                            1592
GGG CAA GAT GAT AAG GTT GAG CCA GAT GAA GAA GAC ATT TGG AAT TAT TTA CCA AGT TCA
 G   Q   D   D   K   V   E   P   D   E   E   D   I   W   N   Y   L   P   S   S
1622                                            1652
AGT TCA CAA CAA GAA GAT TCA TCA CGT GCT TTG AAA AAA AAT ACT AAT TCT GAG AAG GCG
 S   S   Q   Q   E   D   S   S   R   A   L   K   K   N   T   N   S   E   K   A
1682                                            1712
AAC ATC CAA GCA AAG AAC GAT GAA ACC TAT CTG TTT CTT CAG GAT CAG GAT GAA AGC GCT
 N   I   Q   A   K   N   D   E   T   Y   L   F   L   Q   D   Q   D   E   S   A
1742/581                                        1772
GAT TCG CAT CAC CAT GAC GAG TTA GGT TCA GAA ATC ACT TTG GCT GAC AAT AAG TTT TCT
 D   S   H   H   H   D   E   L   G   S   E   I   T   L   A   D   N   K   F   S
1802                                            1832/611
TAT TTG CCC CCA ACT CTA GAA GAG TTG ATG GAA GAG CAG GAC TGT AAC AAT GGC AGA TCT
 Y   L   P   P   T   L   E   E   L   M   E   E   Q   D   C   N   N   G   R   S
1862                                            1892
TTT AAA AAT TTC ATG TTT TCC AAC GAT ACC GGT ATT GAC GGT AGT GCC GGT ACT GAT GAC
 F   K   N   F   M   F   S   N   D   T   G   I   D   G   S   A   G   T   D   D
1922                                            1952
GAC TAC ACC AAA GTT CTG AAA TCC AAA AAA ATT TCT ACG TCG AAG TCG AAC GCT AAC CTT
 D   Y   T   K   V   L   K   S   K   K   I   S   T   S   K   S   N   A   N   L
1982                                            2012
TAT GAC TTA AAC GAT AAC AAC AAT GAT GCA ACT GCC ACC AAT GAA CTT GAT CAA AGC AGT
 Y   D   L   N   D   N   N   N   D   A   T   A   T   N   E   L   D   Q   S   S
2042                                            2072/691
TTC ATC GAC GAC CTT GAC GAA GAT GTC GAT TTT TTA Aag gta caa gta ttt tga aat agg
 F   I   D   D   L   D   E   D   V   D   F   L   K   V   Q   V   F   *
2102                                            2132
cat gtt gca ata aaa cga aaa caa cta aaa atc acg aaa aca aaa tga tat tat aca ata
2162                                            2192
aaa aat tct tat tat ggg taa tga tag tat tct tcg cct gct tag gcg tcc ttt tcc ttc
```

```
2222                              2252
aac aac aaa aat tcc aaa aaa aaa aag taa aaa aac aaa act ttg att gtt ttt taa tga 2282                              2312
tgt taa tga ttt ttt ttt tct ttc ttt atc ata aaa aaa aag tta aaa tga aaa aca aat 2342                              2372
atg ggt ctg gaa ggc cat tat ttt ttt ttt att tat ata ccg ttt ctg gta ctt agt tat 2402                              2432
tta ttc tca tac ata cac tat att caa att acc taa gag cat ttt cac ata tcc gtt tac 2462                              2492
ttt cat ttt ttt ttt ttt tgc ttc ctt ttt aca tat ctt ccg tat atc aca tca cgt tta 2522                              2552
cgc gta tgg tga aac acg tca aga gaa aaa tga taa aat caa att ttg att tac atc agg 2582                              2612
ctc cac agg aca ggg aaa tct atc tag tga ggc gat aac tgt agt tcg atg tac tca ttt 2642                              2672
gaa ctg gac aaa ttg aaa att gag ctg aaa aca tgg gag cat gat ttc att gat aaa aat 2702                              2732
aaa agg gaa ccc aca agg gat gac atc aag agc ctg cgg act gtt cgg cag atg tat aaa 2762                              2792/931
caa tat tcc aca ctg aag aag aaa caa tct ttg caa cga caa aaa gtt gac act caa gag 2822                              2852
tcg gtt gaa ctc ccg gca cat aaa aaa gac cac gac gaa gtc gta gag ata ggc cct act 2882                              2912
ccc caa gtt tac ggt aag gcg att agt atc ttt gac atg aat ttg tcg cct ata aag cct 2942                              2972
ata tac atg aca ttc aca aat aat att gat gtt aac aat gat aac tcc aag aca att tct 3002                              3032
aat gaa tct tct cca cga aaa act att ctc cta aaa tcg tcg cct gca gga att cga tat 3062
caa gct tat cga tac cgt cga
```

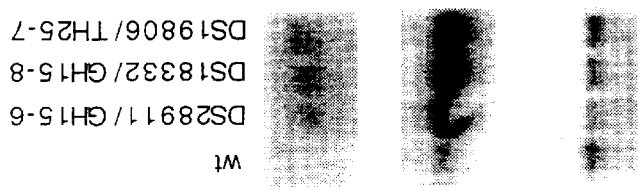
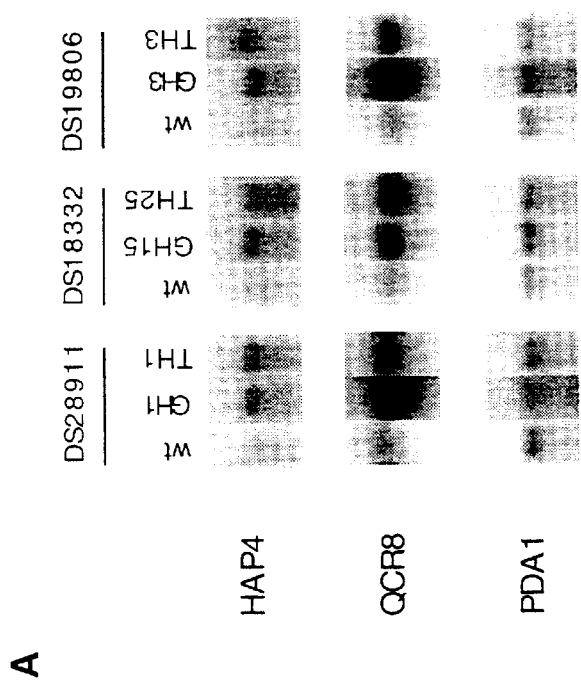
Figure 17

SEQUENCE LISTING

<160> NUMBER OF SEQ ID NOS: 9

<210> SEQ ID NO 1
<211> LENGTH: 1198
<212> TYPE: DNA
<213> ORGANISM: Artificial Sequence
<220> FEATURE:
<223> OTHER INFORMATION: Description of Artificial Sequence: DNA
      construct encoding HAP2
<220> FEATURE:
<221> NAME/KEY: CDS
<222> LOCATION: (201)..(995)

<400> SEQUENCE: 1

```
tcgttattta gcaatcttac ccggaaaact tcttgtatcg taacattaat tctcccttac      60
aaggggacct cgatgaataa ataaagtgtt tgtgttgaag gtacttgcaa aagggcaact     120
cactgtcgtt tataatttga tttactaatc gcatctgtat ttggaaaagc atttcttttt    180
ggaagaggaa caagaacgcc atg tca gca gac gaa acg gat gcg aaa ttt cat     233
                         Met Ser Ala Asp Glu Thr Asp Ala Lys Phe His
                           1               5                  10 cca tta gaa aca gat ctg caa tct gat aca gcg gct gca aca tca acg       281
Pro Leu Glu Thr Asp Leu Gln Ser Asp Thr Ala Ala Ala Thr Ser Thr
             15                  20                  25 gca gca gct tca cgc agt ccc tct ctt caa gag aag ccc ata gag atg       329
Ala Ala Ala Ser Arg Ser Pro Ser Leu Gln Glu Lys Pro Ile Glu Met
         30                  35                  40 ccc ttg gat atg gga aaa gcg cct tct cca aga ggc gaa gat caa cgg       377
Pro Leu Asp Met Gly Lys Ala Pro Ser Pro Arg Gly Glu Asp Gln Arg
     45                  50                  55 gtt aca aat gaa gaa gat ttg ttt ttg ttt aac aga ttg cgg gca tca       425
Val Thr Asn Glu Glu Asp Leu Phe Leu Phe Asn Arg Leu Arg Ala Ser
 60                  65                  70                  75 cag aat aga gtt atg gac tcc ttg gaa cca caa caa cag tca cag tat       473
Gln Asn Arg Val Met Asp Ser Leu Glu Pro Gln Gln Gln Ser Gln Tyr
                 80                  85                  90 aca tct tcc agt gtc agt acg atg gaa cca tct gcc gac ttt act agt       521
Thr Ser Ser Ser Val Ser Thr Met Glu Pro Ser Ala Asp Phe Thr Ser
             95                 100                 105 ttc tct gca gtg act act tta ccg cct cct cct cat caa caa caa cag       569
Phe Ser Ala Val Thr Thr Leu Pro Pro Pro Pro His Gln Gln Gln Gln
         110                 115                 120 caa caa cag cag cag cag cag cag cag caa ttg gtg gtt caa gcc cag       617
Gln Gln Gln Gln Gln Gln Gln Gln Gln Leu Val Val Gln Ala Gln
     125                 130                 135 tac acc caa aat caa cca aac ttg caa agc gat gtt tta gga acc gct       665
Tyr Thr Gln Asn Gln Pro Asn Leu Gln Ser Asp Val Leu Gly Thr Ala
140                 145                 150                 155 ata gca gag caa cca ttt tat gtt aat gcc aag cag tac tac cga att       713
Ile Ala Glu Gln Pro Phe Tyr Val Asn Ala Lys Gln Tyr Tyr Arg Ile
                 160                 165                 170 ttg aaa agg cga tat gca aga gct aaa cta gag gaa aag cta cga ata       761
Leu Lys Arg Arg Tyr Ala Arg Ala Lys Leu Glu Glu Lys Leu Arg Ile
             175                 180                 185 tca aga gaa cga aag cca tac tta cac gaa tct cga cat aaa cat gcg       809
Ser Arg Glu Arg Lys Pro Tyr Leu His Glu Ser Arg His Lys His Ala
         190                 195                 200 atg cga aga cct cgt ggt gaa ggt ggg agg ttc ttg aca gcc gct gag       857
Met Arg Arg Pro Arg Gly Glu Gly Gly Arg Phe Leu Thr Ala Ala Glu
     205                 210                 215
```

```
atc aaa gcc atg aaa tcg aag aaa agt ggg gct agc gat gat cct gac      905
Ile Lys Ala Met Lys Ser Lys Lys Ser Gly Ala Ser Asp Asp Pro Asp
220                 225                 230                 235 gat agt cat gag gat aaa aaa atc act act aaa ata ata caa gaa cag      953
Asp Ser His Glu Asp Lys Lys Ile Thr Thr Lys Ile Ile Gln Glu Gln
                240                 245                 250 ccg cat gct act tcc acc gca gct gca gca gac aaa aaa aca              995
Pro His Ala Thr Ser Thr Ala Ala Ala Ala Asp Lys Lys Thr
                255                 260                 265 taattttgta atattccaat gttaatatca ttcctaaaag aactaaaagt gccctcttat   1055
accacatggt atccatatgg cctatttaat ctgaatcaat atgtatatgt acttttacca   1115
atctcgtttc gtttcgtttc gtttcatttc taacagacct atgtactccg ctggaaaaga   1175
aaccatattg cgatcgtatt tac                                           1198

<210> SEQ ID NO 2
<211> LENGTH: 265
<212> TYPE: PRT
<213> ORGANISM: Artificial Sequence
<220> FEATURE:
<223> OTHER INFORMATION: Description of Artificial Sequence: HAP2

<400> SEQUENCE: 2

Met Ser Ala Asp Glu Thr Asp Ala Lys Phe His Pro Leu Glu Thr Asp
  1               5                  10                  15

Leu Gln Ser Asp Thr Ala Ala Thr Ser Thr Ala Ala Ser Arg
                 20                  25                  30

Ser Pro Ser Leu Gln Glu Lys Pro Ile Glu Met Pro Leu Asp Met Gly
             35                  40                  45

Lys Ala Pro Ser Pro Arg Gly Glu Asp Gln Arg Val Thr Asn Glu Glu
         50                  55                  60

Asp Leu Phe Leu Phe Asn Arg Leu Arg Ala Ser Gln Asn Arg Val Met
 65                  70                  75                  80

Asp Ser Leu Glu Pro Gln Gln Gln Ser Gln Tyr Thr Ser Ser Val
                 85                  90                  95

Ser Thr Met Glu Pro Ser Ala Asp Phe Thr Ser Phe Ser Ala Val Thr
                100                 105                 110

Thr Leu Pro Pro Pro His Gln Gln Gln Gln Gln Gln Gln Gln
            115                 120                 125

Gln Gln Gln Gln Gln Leu Val Val Gln Ala Gln Tyr Thr Gln Asn Gln
        130                 135                 140

Pro Asn Leu Gln Ser Asp Val Leu Gly Thr Ala Ile Ala Glu Gln Pro
145                 150                 155                 160

Phe Tyr Val Asn Ala Lys Gln Tyr Tyr Arg Ile Leu Lys Arg Arg Tyr
                165                 170                 175

Ala Arg Ala Lys Leu Glu Glu Lys Leu Arg Ile Ser Arg Glu Arg Lys
            180                 185                 190

Pro Tyr Leu His Glu Ser Arg His Lys His Ala Met Arg Arg Pro Arg
        195                 200                 205

Gly Glu Gly Gly Arg Phe Leu Thr Ala Ala Glu Ile Lys Ala Met Lys
    210                 215                 220

Ser Lys Lys Ser Gly Ala Ser Asp Asp Pro Asp Asp Ser His Glu Asp
225                 230                 235                 240
```

```
Lys Lys Ile Thr Thr Lys Ile Ile Gln Glu Gln Pro His Ala Thr Ser
                245                 250                 255

Thr Ala Ala Ala Ala Asp Lys Lys Thr
                260                 265

<210> SEQ ID NO 3
<211> LENGTH: 835
<212> TYPE: DNA
<213> ORGANISM: Artificial Sequence
<220> FEATURE:
<223> OTHER INFORMATION: Description of Artificial Sequence: DNA
      construct encoding HAP3
<220> FEATURE:
<221> NAME/KEY: CDS
<222> LOCATION: (201)..(632)

<400> SEQUENCE: 3
caaaccttct gccaaaatat agcacaatag aagtaccata ttacgttcga tgccacgaca      60
atatcgcgct acgtgcgttt tttggtccgc tctttcagac taagtaaaaa aagagctgcg     120
aatagtagct ttccgccaat caaactcaag agcaggacta agctagatag taacacaagt     180
ggcacaaacc tctcgagaat atg aat acc aac gag tcc gaa cat gtt agc aca    233
                       Met Asn Thr Asn Glu Ser Glu His Val Ser Thr
                         1               5                  10 agc cca gag gat act cag gag aac ggt gga aac gct agc tcc agc ggc       281
Ser Pro Glu Asp Thr Gln Glu Asn Gly Gly Asn Ala Ser Ser Ser Gly
             15                  20                  25 agt ttg cag caa att tcc acg cta aga gag cag gac aga tgg cta ccc       329
Ser Leu Gln Gln Ile Ser Thr Leu Arg Glu Gln Asp Arg Trp Leu Pro
         30                  35                  40 atc aac aat gta gcg cga ctc atg aag aat act ctc cca ccg agt gct       377
Ile Asn Asn Val Ala Arg Leu Met Lys Asn Thr Leu Pro Pro Ser Ala
     45                  50                  55 aag gta tcg aaa gat gcg aaa gag tgc atg cag gag tgt gtc agt gag       425
Lys Val Ser Lys Asp Ala Lys Glu Cys Met Gln Glu Cys Val Ser Glu
 60                  65                  70                  75 ctc att tct ttt gtg act agc gag gcc agc gat cga tgc gct gct gac       473
Leu Ile Ser Phe Val Thr Ser Glu Ala Ser Asp Arg Cys Ala Ala Asp
                 80                  85                  90 aaa aga aag acg ata aac ggg gaa gac att ctc ata tca ttg cac gcc       521
Lys Arg Lys Thr Ile Asn Gly Glu Asp Ile Leu Ile Ser Leu His Ala
             95                 100                 105 tta gga ttc gag aac tat gca gag gtg ttg aaa atc tac ttg gct aaa       569
Leu Gly Phe Glu Asn Tyr Ala Glu Val Leu Lys Ile Tyr Leu Ala Lys
         110                 115                 120 tac agg caa caa cag gcg ctg aag aat caa cta atg tat gag cag gac       617
Tyr Arg Gln Gln Gln Ala Leu Lys Asn Gln Leu Met Tyr Glu Gln Asp
     125                 130                 135 gac gaa gag gtg cct tgagaagaca aaaccaggtg gtagatcgca aaagttgcta      672
Asp Glu Glu Val Pro
140 gctgtcagga tggaatagca cggggctatt tcctgctggt cgttggttct cgtgtaatta     732 atgaatgtaa cgatatagat aatattttat tgttagtgtg taatgtattc aatgtaatgt     792 atgggtgctt tgtaaagggt gtatgatgtt tgccaccgga agg                       835

<210> SEQ ID NO 4
<211> LENGTH: 144
<212> TYPE: PRT
<213> ORGANISM: Artificial Sequence
<220> FEATURE:
<223> OTHER INFORMATION: Description of Artificial Sequence: HAP3
```

-continued

```
<400> SEQUENCE: 4

Met Asn Thr Asn Glu Ser Glu His Val Ser Thr Ser Pro Glu Asp Thr
  1               5                  10                  15

Gln Glu Asn Gly Gly Asn Ala Ser Ser Ser Gly Ser Leu Gln Gln Ile
             20                  25                  30

Ser Thr Leu Arg Glu Gln Asp Arg Trp Leu Pro Ile Asn Asn Val Ala
         35                  40                  45

Arg Leu Met Lys Asn Thr Leu Pro Pro Ser Ala Lys Val Ser Lys Asp
     50                  55                  60

Ala Lys Glu Cys Met Gln Glu Cys Val Ser Glu Leu Ile Ser Phe Val
 65                  70                  75                  80

Thr Ser Glu Ala Ser Asp Arg Cys Ala Ala Asp Lys Arg Lys Thr Ile
                 85                  90                  95

Asn Gly Glu Asp Ile Leu Ile Ser Leu His Ala Leu Gly Phe Glu Asn
                100                 105                 110

Tyr Ala Glu Val Leu Lys Ile Tyr Leu Ala Lys Tyr Arg Gln Gln Gln
            115                 120                 125

Ala Leu Lys Asn Gln Leu Met Tyr Glu Gln Asp Asp Glu Glu Val Pro
        130                 135                 140

<210> SEQ ID NO 5
<211> LENGTH: 2065
<212> TYPE: DNA
<213> ORGANISM: Artificial Sequence
<220> FEATURE:
<223> OTHER INFORMATION: Description of Artificial Sequence: DNA
      construct encoding HAP4
<220> FEATURE:
<221> NAME/KEY: CDS
<222> LOCATION: (201)..(1862)

<400> SEQUENCE: 5
taaaggaacc agaaaaataa aaaagggtca ttatttattt gagcagatca ttatcaaacg      60
cataggaaga gaaaaacac agttttattt tttttccaca catatttatt ggtctcctag     120
tacatcaaag agcattttaa tgggttgctg atttgtttta cctacatttt ctagtacaaa    180
aaaaaaacaa aaaaagaatc atg acc gca aag act ttt cta cta cag gcc tcc   233
                        Met Thr Ala Lys Thr Phe Leu Leu Gln Ala Ser
                         1               5                  10 gct agt cgc cct cgt agt aac cat ttt aaa aat gag cat aat aat att     281
Ala Ser Arg Pro Arg Ser Asn His Phe Lys Asn Glu His Asn Asn Ile
             15                  20                  25 cca ttg gcg cct gta ccg atc gcc cca aat acc aac cat cat aac aat     329
Pro Leu Ala Pro Val Pro Ile Ala Pro Asn Thr Asn His His Asn Asn
         30                  35                  40 agt tcg ctg gaa ttc gaa aac gat ggc agt aaa aag aag aag aag tct     377
Ser Ser Leu Glu Phe Glu Asn Asp Gly Ser Lys Lys Lys Lys Lys Ser
     45                  50                  55 agc ttg gtg gtt aga act tca aaa cat tgg gtt ttg ccc cca aga cca     425
Ser Leu Val Val Arg Thr Ser Lys His Trp Val Leu Pro Pro Arg Pro
 60                  65                  70                  75 aga cct ggt aga aga tca tct tct cac aac act cta cct gcc aac aac    473
Arg Pro Gly Arg Arg Ser Ser Ser His Asn Thr Leu Pro Ala Asn Asn
                 80                  85                  90
```

-continued

| | |
|---|---|
| acc aat aat att tta aat gtt ggc cct aac agc agg aac agt agt aat<br>Thr Asn Asn Ile Leu Asn Val Gly Pro Asn Ser Arg Asn Ser Ser Asn<br>                95                        100                      105 | 521 |
| aat aat aat aat aat aac atc att tcg aat agg aaa caa gct tcc aaa<br>Asn Asn Asn Asn Asn Asn Ile Ile Ser Asn Arg Lys Gln Ala Ser Lys<br>            110                      115                      120 | 569 |
| gaa aag agg aaa ata cca aga cat atc cag aca atc gat gaa aag cta<br>Glu Lys Arg Lys Ile Pro Arg His Ile Gln Thr Ile Asp Glu Lys Leu<br>        125                      130                      135 | 617 |
| ata aac gac tcg aat tac ctc gca ttt ttg aag ttc gat gac ttg gaa<br>Ile Asn Asp Ser Asn Tyr Leu Ala Phe Leu Lys Phe Asp Asp Leu Glu<br>140                      145                      150                      155 | 665 |
| aat gaa aag ttt cat tct tct gcc tcc tcc att tca tct cca tct tat<br>Asn Glu Lys Phe His Ser Ser Ala Ser Ser Ile Ser Ser Pro Ser Tyr<br>                160                      165                      170 | 713 |
| tca tct cca tct ttt tca agt tat aga aat aga aaa aaa tca gaa ttc<br>Ser Ser Pro Ser Phe Ser Ser Tyr Arg Asn Arg Lys Lys Ser Glu Phe<br>            175                      180                      185 | 761 |
| atg gac gat gaa agc tgc acc gat gtg gaa acc att gct gct cac aac<br>Met Asp Asp Glu Ser Cys Thr Asp Val Glu Thr Ile Ala Ala His Asn<br>        190                      195                      200 | 809 |
| agt ctg cta aca aaa aac cat cat ata gat tct tct tca aat gtt cac<br>Ser Leu Leu Thr Lys Asn His His Ile Asp Ser Ser Ser Asn Val His<br>        205                      210                      215 | 857 |
| gca cca ccc acg aaa aaa tca aag ttg aac gac ttt gat tta ttg tcc<br>Ala Pro Pro Thr Lys Lys Ser Lys Leu Asn Asp Phe Asp Leu Leu Ser<br>220                      225                      230                      235 | 905 |
| tta tct tcc aca tct tca tcg gcc act ccg gtc cca cag ttg aca aaa<br>Leu Ser Ser Thr Ser Ser Ser Ala Thr Pro Val Pro Gln Leu Thr Lys<br>                240                      245                      250 | 953 |
| gat ttg aac atg aac cta aat ttt cat aag atc cct cat aag gct tca<br>Asp Leu Asn Met Asn Leu Asn Phe His Lys Ile Pro His Lys Ala Ser<br>            255                      260                      265 | 1001 |
| ttc cct gat tct cca gca gat ttc tct cca gca gat tca gtc tcg ttg<br>Phe Pro Asp Ser Pro Ala Asp Phe Ser Pro Ala Asp Ser Val Ser Leu<br>        270                      275                      280 | 1049 |
| att aga aac cac tcc ttg cct act aat ttg caa gtt aag gac aaa att<br>Ile Arg Asn His Ser Leu Pro Thr Asn Leu Gln Val Lys Asp Lys Ile<br>285                      290                      295 | 1097 |
| gag gat ttg aac gag att aaa ttc ttt aac gat ttc gag aaa ctt gag<br>Glu Asp Leu Asn Glu Ile Lys Phe Phe Asn Asp Phe Glu Lys Leu Glu<br>300                      305                      310                      315 | 1145 |
| ttt ttc aat aag tat gcc aaa gtc aac acg aat aac gac gtt aac gaa<br>Phe Phe Asn Lys Tyr Ala Lys Val Asn Thr Asn Asn Asp Val Asn Glu<br>                320                      325                      330 | 1193 |
| aat aat gat ctc tgg aat tct tac tta cag tct atg gac gat aca aca<br>Asn Asn Asp Leu Trp Asn Ser Tyr Leu Gln Ser Met Asp Asp Thr Thr<br>            335                      340                      345 | 1241 |
| ggt aag aac agt ggc aat tac caa caa gtg gac aat gac gat aat atg<br>Gly Lys Asn Ser Gly Asn Tyr Gln Gln Val Asp Asn Asp Asp Asn Met<br>        350                      355                      360 | 1289 |

-continued

| | | | | | | | | | | | | | | | |
|---|---|---|---|---|---|---|---|---|---|---|---|---|---|---|---|
| tct | tta | ttg | aat | ctg | cca | att | ttg | gag | gaa | acc | gta | tct | tca | ggg | caa | 1337 |
| Ser | Leu | Leu | Asn | Leu | Pro | Ile | Leu | Glu | Glu | Thr | Val | Ser | Ser | Gly | Gln | |
| | 365 | | | | 370 | | | | | 375 | | | | | | |

| gat | gat | aag | gtt | gag | cca | gat | gaa | gaa | gac | att | tgg | aat | tat | tta | cca | 1385 |
| Asp | Asp | Lys | Val | Glu | Pro | Asp | Glu | Glu | Asp | Ile | Trp | Asn | Tyr | Leu | Pro |
| 380 | | | | | 385 | | | | | 390 | | | | | 395 |

| agt | tca | agt | tca | caa | caa | gaa | gat | tca | tca | cgt | gct | ttg | aaa | aaa | aat | 1433 |
| Ser | Ser | Ser | Ser | Gln | Gln | Glu | Asp | Ser | Ser | Arg | Ala | Leu | Lys | Lys | Asn |
| | | | | 400 | | | | | 405 | | | | | 410 | |

| act | aat | tct | gag | aag | gcg | aac | atc | caa | gca | aag | aac | gat | gaa | acc | tat | 1481 |
| Thr | Asn | Ser | Glu | Lys | Ala | Asn | Ile | Gln | Ala | Lys | Asn | Asp | Glu | Thr | Tyr |
| | | 415 | | | | | 420 | | | | | 425 | | | |

| ctg | ttt | ctt | cag | gat | cag | gat | gaa | agc | gct | gat | tcg | cat | cac | cat | gac | 1529 |
| Leu | Phe | Leu | Gln | Asp | Gln | Asp | Glu | Ser | Ala | Asp | Ser | His | His | His | Asp |
| | 430 | | | | | 435 | | | | | 440 | | | | |

| gag | tta | ggt | tca | gaa | atc | act | ttg | gct | gac | aat | aag | ttt | tct | tat | ttg | 1577 |
| Glu | Leu | Gly | Ser | Glu | Ile | Thr | Leu | Ala | Asp | Asn | Lys | Phe | Ser | Tyr | Leu |
| | | 445 | | | | | 450 | | | | | 455 | | | |

| ccc | cca | act | cta | gaa | gag | ttg | atg | gaa | gag | cag | gac | tgt | aac | aat | ggc | 1625 |
| Pro | Pro | Thr | Leu | Glu | Glu | Leu | Met | Glu | Glu | Gln | Asp | Cys | Asn | Asn | Gly |
| 460 | | | | | 465 | | | | | 470 | | | | | 475 |

| aga | tct | ttt | aaa | aat | ttc | atg | ttt | tcc | aac | gat | acc | ggt | att | gac | ggt | 1673 |
| Arg | Ser | Phe | Lys | Asn | Phe | Met | Phe | Ser | Asn | Asp | Thr | Gly | Ile | Asp | Gly |
| | | | 480 | | | | | 485 | | | | | 490 | | |

| agt | gcc | ggt | act | gat | gac | gac | tac | acc | aaa | gtt | ctg | aaa | tcc | aaa | aaa | 1721 |
| Ser | Ala | Gly | Thr | Asp | Asp | Asp | Tyr | Thr | Lys | Val | Leu | Lys | Ser | Lys | Lys |
| | | 495 | | | | | 500 | | | | | 505 | | | |

| att | tct | acg | tcg | aag | tcg | aac | gct | aac | ctt | tat | gac | tta | aac | gat | aac | 1769 |
| Ile | Ser | Thr | Ser | Lys | Ser | Asn | Ala | Asn | Leu | Tyr | Asp | Leu | Asn | Asp | Asn |
| | | 510 | | | | | 515 | | | | | 520 | | | |

| aac | aat | gat | gca | act | gcc | acc | aat | gaa | ctt | gat | caa | agc | agt | ttc | atc | 1817 |
| Asn | Asn | Asp | Ala | Thr | Ala | Thr | Asn | Glu | Leu | Asp | Gln | Ser | Ser | Phe | Ile |
| 525 | | | | | 530 | | | | | 535 | | | | | |

| gac | gac | ctt | gac | gaa | gat | gtc | gat | ttt | tta | aag | gta | caa | gta | ttt | | 1862 |
| Asp | Asp | Leu | Asp | Glu | Asp | Val | Asp | Phe | Leu | Lys | Val | Gln | Val | Phe | |
| 540 | | | | 545 | | | | | 550 | | | | | | | tgaaataggc atgttgcaat aaaacgaaaa caactaaaaa tcacgaaaac aaaatgatat 1922 tatacaataa aaaattctta ttatgggtaa tgatagtatt cttcgcctgc ttaggcgtcc 1982 ttttccttca acaacaaaaa ttccaaaaaa aaaagtaaa aaaacaaaac tttgattgtt 2042 ttttaatgat gttaatgatt ttt 2065

<210> SEQ ID NO 6
<211> LENGTH: 554
<212> TYPE: PRT
<213> ORGANISM: Artificial Sequence
<220> FEATURE:
<223> OTHER INFORMATION: Description of Artificial Sequence: HAP4

<400> SEQUENCE: 6

Met Thr Ala Lys Thr Phe Leu Leu Gln Ala Ser Ala Ser Arg Pro Arg
1               5                   10                  15

Ser Asn His Phe Lys Asn Glu His Asn Asn Ile Pro Leu Ala Pro Val
            20                  25                  30

Pro Ile Ala Pro Asn Thr Asn His His Asn Asn Ser Ser Leu Glu Phe
        35                  40                  45

Glu Asn Asp Gly Ser Lys Lys Lys Lys Ser Ser Leu Val Val Arg
    50                  55                  60

-continued

```
Thr Ser Lys His Trp Val Leu Pro Pro Arg Pro Arg Pro Gly Arg Arg
 65                  70                  75                  80

Ser Ser Ser His Asn Thr Leu Pro Ala Asn Asn Thr Asn Asn Ile Leu
                 85                  90                  95

Asn Val Gly Pro Asn Ser Arg Asn Ser Asn Asn Asn Asn Asn Asn Asn
            100                 105                 110

Asn Ile Ile Ser Asn Arg Lys Gln Ala Ser Lys Glu Lys Arg Lys Ile
            115                 120                 125

Pro Arg His Ile Gln Thr Ile Asp Glu Lys Leu Ile Asn Asp Ser Asn
        130                 135                 140

Tyr Leu Ala Phe Leu Lys Phe Asp Asp Leu Glu Asn Glu Lys Phe His
145                 150                 155                 160

Ser Ser Ala Ser Ser Ile Ser Ser Pro Ser Tyr Ser Pro Ser Ser Phe
                165                 170                 175

Ser Ser Tyr Arg Asn Arg Lys Lys Ser Glu Phe Met Asp Asp Glu Ser
            180                 185                 190

Cys Thr Asp Val Glu Thr Ile Ala Ala His Asn Ser Leu Leu Thr Lys
        195                 200                 205

Asn His His Ile Asp Ser Ser Ser Asn Val His Ala Pro Pro Thr Lys
210                 215                 220

Lys Ser Lys Leu Asn Asp Phe Asp Leu Leu Ser Leu Ser Ser Thr Ser
225                 230                 235                 240

Ser Ser Ala Thr Pro Val Pro Gln Leu Thr Lys Asp Leu Asn Met Asn
                245                 250                 255

Leu Asn Phe His Lys Ile Pro His Lys Ala Ser Phe Pro Asp Ser Pro
            260                 265                 270

Ala Asp Phe Ser Pro Ala Asp Ser Val Ser Leu Ile Arg Asn His Ser
        275                 280                 285

Leu Pro Thr Asn Leu Gln Val Lys Asp Lys Ile Glu Asp Leu Asn Glu
    290                 295                 300

Ile Lys Phe Phe Asn Asp Phe Glu Lys Leu Glu Phe Phe Asn Lys Tyr
305                 310                 315                 320

Ala Lys Val Asn Thr Asn Asn Asp Val Asn Glu Asn Asn Asp Leu Trp
                325                 330                 335

Asn Ser Tyr Leu Gln Ser Met Asp Asp Thr Thr Gly Lys Asn Ser Gly
            340                 345                 350

Asn Tyr Gln Gln Val Asp Asn Asp Asp Asn Met Ser Leu Leu Asn Leu
        355                 360                 365

Pro Ile Leu Glu Glu Thr Val Ser Ser Gly Gln Asp Asp Lys Val Glu
    370                 375                 380

Pro Asp Glu Glu Asp Ile Trp Asn Tyr Leu Pro Ser Ser Ser Ser Gln
385                 390                 395                 400

Gln Glu Asp Ser Ser Arg Ala Leu Lys Lys Asn Thr Asn Ser Glu Lys
                405                 410                 415

Ala Asn Ile Gln Ala Lys Asn Asp Glu Thr Tyr Leu Phe Leu Gln Asp
            420                 425                 430

Gln Asp Glu Ser Ala Asp Ser His His Asp Glu Leu Gly Ser Glu
        435                 440                 445

Ile Thr Leu Ala Asp Asn Lys Phe Ser Tyr Leu Pro Pro Thr Leu Glu
    450                 455                 460

Glu Leu Met Glu Glu Gln Asp Cys Asn Asn Gly Arg Ser Phe Lys Asn
465                 470                 475                 480
```

-continued

```
Phe Met Phe Ser Asn Asp Thr Gly Ile Asp Gly Ser Ala Gly Thr Asp
            485                 490                 495

Asp Asp Tyr Thr Lys Val Leu Lys Ser Lys Lys Ile Ser Thr Ser Lys
        500                 505                 510

Ser Asn Ala Asn Leu Tyr Asp Leu Asn Asp Asn Asn Asn Asp Ala Thr
        515                 520                 525

Ala Thr Asn Glu Leu Asp Gln Ser Ser Phe Ile Asp Asp Leu Asp Glu
    530                 535                 540

Asp Val Asp Phe Leu Lys Val Gln Val Phe
545                 550

<210> SEQ ID NO 7
<211> LENGTH: 2394
<212> TYPE: DNA
<213> ORGANISM: Artificial Sequence
<220> FEATURE:
<223> OTHER INFORMATION: Description of Artificial Sequence: DNA
      construct consisting of the ADH1 promoter fused to the
      coding region of HAP4

<400> SEQUENCE: 7
atccttttgt tgtttccggg tgtacaatat ggacttcctc ttttctggca accaaaccca      60
tacatcggga ttcctataat accttcgttg gtctccctaa catgtaggtg gcggaggggga    120
gatatacaat agaacagata ccagacaaga cataatgggc taaacaagac tacaccaatt    180
acactgcctc attgatggtg gtacataacg aactaatact gtagccctag acttgatagc    240
catcatcata tcgaagtttc actacccttt ttccatttgc catctattga agtaataata    300
ggcgcatgca acttcttttc tttttttttc ttttctctct ccccgttgt tgtctcacca     360
tatccgcaat gacaaaaaaa atgatggaag acactaaagg aaaaaattaa cgacaaagac    420
agcaccaaca gatgtcgttg ttccagagct gatgagggg atcttcgaac acacgaaact     480
ttttccttcc ttcattcacg cacactactc tctaatgagc aacggtatac ggccttcctt    540
ccagttactt gaatttgaaa taaaaaaagt ttgccgcttt gctatcaagt ataaatagac    600
ctgcaattat taatcttttg tttcctcgtc attgttctcg ttccctttct tccttgtttc    660
tttttctgca caatatttca agctatacca agcatacaat caaggaattc gagctcgccc    720
catgaccgca aagactttc tactacaggc ctccgctagt cgccctcgta gtaaccattt      780
taaaaatgag cataataata ttccattggc gcctgtaccg atcgcccaa ataccaacca     840
tcataacaat agttcgctgg aattcgaaaa cgatggcagt aaaaagaaga agaagtctag    900
cttggtggtt agaacttcaa acattgggt tttgccccca agaccaagac ctggtagaag     960
atcatcttct cacaacactc tacctgccaa caacaccaat aatattttaa atgttggccc   1020
taacagcagg aacagtagta ataataataa taataataac atcatttcga ataggaaaca   1080
agcttccaaa gaaaagagga aaataccaag acatatccag acaatcgatg aaaagctaat   1140
aaacgactcg aattacctcg cattttgaa gttcgatgac ttggaaaatg aaaagtttcg    1200
ttcttctgcc tcctccattt catctccatc ttattcatct ccatcttttt caagttatag   1260
aaatagaaaa aaatcagaat tcatggacga tgaaagctgc accgatgtgg aaaccattgc   1320
tgctcacaac agtctgctaa caaaaaacca tcatatagat tcttcttcaa atgttcacgc   1380
accacccacg aaaaaatcaa agttgaacga ctttgattta ttgtccttat cttccacatc   1440
ttcatcggcc actccggtcc cacagttgac aaaagatttg aacatgaacc taaattttca   1500
taagatccct cataaggctt cattccctga ttctccagca gatttctctc cagcagattc   1560
```

-continued

```
agtctcgttg attagaaacc actccttgcc tactaatttg caagttaagg acaaaattga    1620
ggatttgaac gagattaaat tctttaacga tttcgagaaa cttgagtttt tcaataagta    1680
tgccaaagtc aacacgaata acgacgttaa cgaaaataat gatctctgga attcttactt    1740
acagtctatg gacgatacaa caggtaagaa cagtggcaat taccaacaag tggacaatga    1800
cgataatatg tctttattga atctgccaat tttggaggaa accgtatctt cagggcaaga    1860
tgataaggtt gagccagatg aagaagacat ttggaattat ttaccaagtt caagttcaca    1920
acaagaagat tcatcacgtg ctttgaaaaa aaatactaat tctgagaagg cgaacatcca    1980
agcaaagaac gatgaaacct atctgtttct tcaggatcag gatgaaagcg ctgattcgca    2040
tcaccatgac gagttaggtt cagaaatcac tttggctgac aataagttttt cttatttgcc    2100 cccaactcta gaagagttga tggaagagca ggactgtaac aatggcagat cttttaaaaa    2160
tttcatgttt tccaacgata ccggtattga cggtagtgcc ggtactgatg acgactacac    2220
caaagttctg aaatccaaaa aaatttctac gtcgaagtcg aacgctaacc tttatgactt    2280
aaacgataac aacaatgatg caactgccac caatgaactt gatcaaagca gtttcatcga    2340
cgaccttgac gaagatgtcg attttttaaa ggtacaagta ttttaagggg atcc          2394
```

<210> SEQ ID NO 8
<211> LENGTH: 3360
<212> TYPE: DNA
<213> ORGANISM: Artificial Sequence
<220> FEATURE:
<223> OTHER INFORMATION: Description of Artificial Sequence: DNA
      construct consisting of the GPD1 promoter fused to the
      coding region of HAP4

<400> SEQUENCE: 8

```
gagctctggg gtttgagcaa gtctaagttt acgtagcata aaaattctcg gattgcgtca      60
aataataaaa aaagtaaccc cacttctact tctacatcgg aaaaacattc cattcacata     120
tcgtctttgg cctatcttgt tttgtcctcg gtagatcagg tcagtacaaa cgcaacacga     180
aagaacaaaa aaagaagaaa acagaaggcc aagacagggt caatgagact gttgtcctcc     240
tactgtccct atgtctctgg ccgatcacgc gccattgtcc ctcagaaaca aatcaaacac     300
ccacaccccg ggcacccaaa gtccccaccc acaccaccaa tacgtaaacg gggcgccccc     360
tgcaggccct cctgcgcgcg gcctcccgcc ttgcttctct ccccttcctt ttcttttttcc    420 agttttccct attttgtccc ttttttccgca caacaagtat cagaatgggt tcatcaaatc    480
tatccaacct aattcgcacg tagactggct tggtattggc agtttcgtag ttatatatat     540
actaccatga gtgaaactgt tacgttacct taaattcttt ctcccttttaa ttttctttta    600 tcttactctc ctacataaga catcaagaaa caattgtata ttgtacaccc cccccctcca     660
caaacacaaa tattgataat ataaagtcta gaactagtgg atccccccat gaccgcaaag     720
acttttctac tacaggcctc cgctagtcgc cctcgtagta accattttaa aaatgagcat     780
aataatattc cattggcgcc tgtaccgatc gccccaaata ccaaccatca taacaatagt     840
tcgctggaat tcgaaaacga tggcagtaaa agaagaagaa agtctagctt ggtggttaga     900
acttcaaaac attgggtttt gcccccaaga ccaagacctg gtagaagatc atcttctcac     960
aacactctac ctgccaacaa caccaataat atttaaatg ttggccctaa cagcaggaac     1020
agtagtaata ataataataa taataacatc atttcgaata ggaaacaagc ttccaaagaa    1080
aagaggaaaa taccaagaca tatccagaca atcgatgaaa agctaataaa cgactcgaat    1140
tacctcgcat ttttgaagtt cgatgacttg gaaaatgaaa agtttcattc ttctgcctcc    1200
```

-continued

```
tccatttcat ctccatctta ttcatctcca tctttttcaa gttatagaaa tagaaaaaaa    1260
tcagaattca tggacgatga aagctgcacc gatgtggaaa ccattgctgc tcacaacagt    1320
ctgctaacaa aaaccatca tatagattct tcttcaaatg ttcacgcacc acccacgaaa    1380
aaatcaaagt tgaacgactt tgatttattg tccttatctt ccacatcttc atcggccact    1440
ccggtcccac agttgacaaa agatttgaac atgaacctaa attttcataa gatccctcat    1500
aaggcttcat tccctgattc tccagcagat ttctctccag cagattcagt ctcgttgatt    1560
agaaaccact ccttgcctac taatttgcaa gttaaggaca aaattgagga tttgaacgag    1620
attaaattct ttaacgattt cgagaaactt gagtttttca ataagtatgc caaagtcaac    1680
acgaataacg acgttaacga aaataatgat ctctggaatt cttacttaca gtctatggac    1740
gatacaacag gtaagaacag tggcaattac caacaagtgg acaatgacga taatatgtct    1800
ttattgaatc tgccaatttt ggaggaaacc gtatcttcag ggcaagatga taaggttgag    1860
ccagatgaag aagacatttg gaattattta ccaagttcaa gttcacaaca agaagattca    1920
tcacgtgctt tgaaaaaaaa tactaattct gagaaggcga acatccaagc aaagaacgat    1980
gaaacctatc tgtttcttca ggatcaggat gaaagcgctg attcgcatca ccatgacgag    2040
ttaggttcag aaatcacttt ggctgacaat aagttttctt atttgccccc aactctagaa    2100
gagttgatgg aagagcagga ctgtaacaat ggcagatctt taaaaatttt catgttttcc    2160
aacgataccg gtattgacgg tagtgccggt actgatgacg actacaccaa agttctgaaa    2220
tccaaaaaaa tttctacgtc gaagtcgaac gctaaccttt atgacttaaa cgataacaac    2280
aatgatgcaa ctgccaccaa tgaacttgat caaagcagtt tcatcgacga ccttgacgaa    2340
gatgtcgatt ttttaaaggt acaagtattt tgaaataggc atgttgcaat aaaacgaaaa    2400
caactaaaaa tcacgaaaac aaaatgatat tatacaataa aaaattctta ttatgggtaa    2460
tgatagtatt cttcgcctgc ttaggcgtcc ttttccttca acaacaaaaa ttccaaaaaa    2520
aaaaagtaaa aaaacaaaac tttgattgtt tttaatgat gttaatgatt ttttttttct    2580
ttctttatca taaaaaaaaa gttaaaatga aaaacaaata tgggtctgga aggccattat    2640 tttttttta tttatatacc gtttctggta cttagttatt tattctcata catacactat    2700
attcaaatta cctaagagca ttttcacata tccgtttact ttcattttttt tttttttgc    2760 ttccttttta catatcttcc gtatatcaca tcacgtttac gcgtatggtg aaacacgtca    2820
agagaaaaat gataaaatca aattttgatt tacatcaggc tccacaggac agggaaatct    2880
atctagtgag gcgataactg tagttcgatg tactcatttg aactggacaa attgaaaatt    2940
gagctgaaaa catgggagca tgatttcatt gataaaaata aagggaacc cacaagggat    3000 gacatcaaga gcctgcggac tgttcggcag atgtataaac aatattccac actgaagaag    3060
aaacaatctt tgcaacgaca aaaagttgac actcaagagt cggttgaact cccggcacat    3120
aaaaaagacc acgacgaagt cgtagagata ggccctactc cccaagttta cggtaaggcg    3180
attagtatct ttgacatgaa tttgtcgcct ataaagccta tatacatgac attcacaaat    3240
aatattgatg ttaacaatga taactccaag acaatttcta atgaatcttc tccacgaaaa    3300
actattctcc taaaatcgtc gcctgcagga attcgatatc aagcttatcg ataccgtcga    3360
```

<210> SEQ ID NO 9
<211> LENGTH: 3081
<212> TYPE: DNA
<213> ORGANISM: Artificial Sequence
<220> FEATURE:
<223> OTHER INFORMATION: Description of Artificial Sequence: DNA
construct consisting of the TEF2 promoter fused to the coding
region of HAP4

<400> SEQUENCE: 9

```
agctcaatgt ttctactcct tttttactct tccagatttt ctcggactcc gcgcatcgcc      60
gtaccacttc aaaacaccca agcacagcat actaaatttc ccctctttct tcctctaggg     120
tgtcgttaat tacccgtact aaaggtttgg aaaagaaaaa agagaccgcc tcgtttcttt     180
ttcttcgtcg aaaaaggcaa taaaaatttt tatcacgttt cttttcttg aaaatttttt      240
tttttgattt ttttctcttt cgatgacctc ccattgatat ttaagttaat aaacggtctt     300
caatttctca agtttcagtt tcattttct tgttctatta caacttttt tacttcttgc       360
tcattagaaa gaaagcatag caatctaatc taagttttaa ttacaaatct agaactagtg     420
gatcccccca tgaccgcaaa gacttttcta ctacaggcct ccgctagtcg ccctcgtagt     480
aaccatttta aaatgagca taataatatt ccattggcgc ctgtaccgat cgccccaaat      540
accaaccatc ataacaatag ttcgctggaa ttcgaaaacc atggcagtaa aaagaagaag     600
aagtctagct tggtggttag aacttcaaaa cattgggttt tgcccccaag accaagacct     660
ggtagaagat catcttctca caacactcta cctgccaaca acaccaataa tatttaaat     720
gttggcccta acagcaggaa cagtagtaat aataataata ataataacat catttcgaat     780
aggaaacaag cttccaaaga aaagaggaaa ataccaagac atatccagac aatcgatgaa     840
aagctaataa acgactcgaa ttacctcgca tttttgaagt tcgatgactt ggaaaatgaa     900
aagtttcatt cttctgcctc ctccatttca tctccatctt attcatctcc atctttttca     960
agttatagaa atagaaaaaa atcagaattc atggacgatg aaagctgcac cgatgtggaa    1020
accattgctg ctcacaacag tctgctaaca aaaaaccatc atatagattc ttcttcaaat    1080
gttcacgcac cacccacgaa aaaatcaaag ttgaacgact tgatttatt gtccttatct    1140
tccacatctt catcggccac tccggtccca cagttgacaa agatttgaa catgaaccta    1200
aattttcata agatccctca taaggcttca ttccctgatt ctccagcaga tttctctcca    1260
gcagattcag tctcgttgat tagaaaccac tccttgccta ctaatttgca agttaaggac    1320
aaaattgagg atttgaacga gattaaattc tttaacgatt tcgagaaact tgagtttttc    1380
aataagtatg ccaaagtcaa cacgaataac gacgttaacg aaaataatga tctctggaat    1440
tcttacttac agtctatgga cgatacaaca ggtaagaaca gtggcaatta ccaacaagtg    1500
gacaatgacg ataatatgtc tttattgaat ctgccaattt tggaggaaac cgtatcttca    1560
gggcaagatg ataaggttga gccagatgaa gaagacattt ggaattattt accaagttca    1620
agttcacaac aagaagattc atcacgtgct ttgaaaaaaa atactaattc tgagaaggcg    1680
aacatccaag caaagaacga tgaaacctat ctgtttcttc aggatcagga tgaaagcgct    1740
gattcgcatc accatgacga gttaggttca gaaatcactt tggctgacaa taagttttct    1800
tatttgcccc caactctaga agagttgatg gaagagcagg actgtaacaa tggcagatct    1860
tttaaaaatt tcatgttttc caacgatacc ggtattgacg gtagtgccgg tactgatgac    1920
gactacacca aagttctgaa atccaaaaaa atttctacgt cgaagtcgaa cgctaacctt    1980
tatgacttaa acgataacaa caatgatgca actgccacca atgaacttga tcaaagcagt    2040
```

-continued

```
ttcatcgacg accttgacga agatgtcgat tttttaaagg tacaagtatt ttgaaatagg    2100
catgttgcaa taaaacgaaa acaactaaaa atcacgaaaa caaaatgata ttatacaata    2160
aaaaattctt attatgggta atgatagtat tcttcgcctg cttaggcgtc cttttccttc    2220
aacaacaaaa attccaaaaa aaaaaagtaa aaaaacaaaa ctttgattgt tttttaatga    2280
tgttaatgat ttttttttc tttctttatc ataaaaaaaa agttaaaatg aaaaacaaat    2340
atgggtctgg aaggccatta tttttttttt atttatatac cgtttctggt acttagttat    2400
ttattctcat acatacacta tattcaaatt acctaagagc attttcacat atccgtttac    2460
tttcattttt ttttttttg cttccttttt acatatcttc cgtatatcac atcacgttta    2520
cgcgtatggt gaaacacgtc aagagaaaaa tgataaaatc aaattttgat ttacatcagg    2580
ctccacagga cagggaaatc tatctagtga ggcgataact gtagttcgat gtactcattt    2640
gaactggaca aattgaaaat tgagctgaaa acatgggagc atgatttcat tgataaaaat    2700
aaaagggaac ccacaaggga tgacatcaag agcctgcgga ctgttcggca gatgtataaa    2760
caatattcca cactgaagaa gaaacaatct ttgcaacgac aaaaagttga cactcaagag    2820
tcggttgaac tcccggcaca taaaaaagac cacgacgaag tcgtagagat aggccctact    2880
ccccaagttt acggtaaggc gattagtatc tttgacatga atttgtcgcc tataaagcct    2940
atatacatga cattcacaaa taatattgat gttaacaatg ataactccaa gacaatttct    3000
aatgaatctt ctccacgaaa aactattctc ctaaaatcgt cgcctgcagg aattcgatat    3060
caagcttatc gataccgtcg a                                             3081
```

METHODS FOR MODULATING METABOLIC PATHWAYS OF MICRO-ORGANISMS AND MICRO-ORGANISMS OBTAINABLE BY SAID METHODS

This application is the U.S. National Phase entry of PCT/NL97/00688 filed Dec. 12, 1997 and has benefit of priority from that filing date.

The present invention relates to the field of biotechnology, in particular to the field of culturing micro-organisms, in particular yeast.

Culturing of micro-organisms is a relatively old technique which is well established and well understood by persons skilled in this art. It usually involves bringing a micro-organism of interest into a culture medium wherein it can survive, grow and divide. The culture medium usually comprises all the necessary nutrients for the micro-organism to be able to do this.

Micro-organisms are cultured for many different purposes. These include the production of biomass, the production of antibiotics, the production of useful proteins expressed by micro-organisms (be it naturally or through genetic engineering), the production of micro-organisms useful themselves (for instance in brewing or baking bread, leavening of dough, etc.) Because of its relatively long history and its many uses the techniques for culturing micro-organisms have been very well optimised, so that further gains in yield or growth rate of the micro-organism to be cultured are difficult to achieve. However, because of the cost of culturing micro-organisms and the large amounts needed, such improvements (however small percentage-wise) remain very desirable.

One of the problems of culturing micro-organisms is that they often show preference for certain carbon sources, which carbon sources do not result in the best yields and/or growth rates of the micro-organism. Often the availability of such a preferred carbon source will lead to repression of the metabolism of other available carbon sources (which other carbon sources often do result in higher yields). For instance, *S. cerevisiae*, as many other micro-organisms, shows marked preferences for certain sources of carbon, nitrogen and energy. One such preference concerns the use of glucose above other fermentable and non-fermentable carbon compounds (see 1,2). This behaviour causes diauxic growth of this yeast when cultured on mixtures of carbon sources that include glucose. Yeast cells growing on glucose display high growth rates, presumably related to the ease with which intermediates can be derived from the catabolism of this sugar. Glucose has radical consequences for the enzyme complement and metabolic patterns in the yeast cell (FIG. 1). During growth on this sugar, enzymes required for metabolism of other carbon sources are either absent or strongly reduced in amount as a result of active degradation of mRNAs or proteins (catabolite inactivation), repressed synthesis of mRNAs (catabolite repression), or both. Such enzymes include permeases and key enzymes involved in the utilization of various sugars, enzymes of gluconeogenesis and the glyoxylate cycle. In addition, synthesis of components of the mitochondrial respiratory chain is repressed, resulting in a low respiratory capacity. Glucose-repressed cells, or cells pulsed briefly with excess glucose produce ethanol by decarboxylation of cytosolic pyruvate and subsequent action of alcohol dehydrogenase. This series of reactions, known as the Crabtree-effect, regenerates cytosolic $NAD^+$ required for glycolysis. Although the basis of the Crabtree response is largely unknown (3), the occurrence of these reactions during large scale production of *S. cerevisiae* is undesirable because it reduces cell yield.

Suppression of ethanol production by yeast cells growing on glucose is currently achieved by limitation of the supply rate of the sugar. This procedure is only partially successful in that incomplete mixing can trigger a short-term Crabtree response. Additionally it suffers from the drawback that cells are forced to grow below their maximum capacity.

These or similar problems occur in many micro-organisms, particularly in eukaryotes, more in particular in yeasts. The present invention provides a general mechanism by which such problems may be solved in that it provides a method for producing a micro-organism of which a metabolic pathway has been modulated, for instance a micro-organism of which the sugar/glucose metabolism has been shifted from aerobic fermentation towards oxidation, comprising providing said micro-organism with the capability of inhibition or circumvention of the repression of the oxidative metabolism of glucose induced by the availability for the micro-organism of said carbon source. Surprisingly we have found that by simply interfering at a single (well-chosen) spot in the complex regulatory mechanisms of metabolic routes in (in particular) eukaryotic micro-organisms, it is possible to redirect said metabolic routes from one mechanism (fermentation) to another (oxidation). Because of the complexity of the regulatory systems surrounding metabolism it is generally believed that interference at a single point would be unlikely to be of any significance (because of all kinds of positive and negative homeostatic mechanisms which would restore the original situation) or would be deleterious if not disastrous (if it were capable of disrupting the feedback-mechanisms). We have found that a simple modification, in particular at the level of transcription activation does lead to the desired switch in metabolic mechanism, without disrupting the metabolism of the micro-organism.

In particular, the invention solves this problem when the preferred carbon source of the micro-organism is glucose, which is the case for many micro-organisms, in particular yeasts. One of the most important yeasts in industry is (of course) *Saccharomyces cerevisiae*. For that reason we have chosen this micro-organism as a model for explaining our invention. Because of its importance it is of course also a highly preferred embodiment of the present invention. Other well known industrial yeast strains such as Hansenula, Kluyveromyces and other strains are of course also within the scope of the present invention.

It will be understood that the result of the preference for glucose leads the metabolism down the aerobic fermentative pathway in many cases, as will be explained below. It will also be clear that for yield in biomass and/or production of useful proteins, etc. the oxidative/gluconeogenesis pathway is to be preferred. This pathway is often part of the metabolism that is repressed when glucose is available and which is used when other carbon sources are available. Thus an important aspect of the present invention is to provide a method according whereby the repressed metabolism is restored to a significant extent by activation of the pathways for metabolism for the non-preferred carbon sources.

It is preferred that said activation is achieved by providing the micro-organism with at least one transcriptional activator for at least one gene encoding an enzyme in said pathways.

A very suitable and preferred way of achieving said activation is one whereby the transcriptional activator is provided by introduction into the micro-organism of a recombinant nucleic acid encoding said activator. Said recombinant nucleic acid is preferably an expression vector. Such a vector may be an autonomously replicating vector, but it is preferred to use vectors that integrate in the host genome. However, it may also be achieved by other means, such as mutation (site directed).

There are two ways of having the transcriptional activator expressed. In one embodiment of the invention the transcriptional activator is constitutively expressed by said micro-organism. In an alternative embodiment the transcriptional activator can be expressed by the micro-organism upon induction, for instance by the presence of glucose. The person skilled in the art will be able to determine which one is to be used for different circumstances and desired end results. In many instances it will be preferred that the vector used to introduce the activator is capable of integration into the genome of the host. In other embodiments a self-replicating vector may be used.

A very efficient way of achieving the derepression of the metabolic pathways other than those active in the presence of glucose is one whereby the transcriptional activator provided is a Hap4 protein or a functional equivalent, derivative or fragment thereof. A functional equivalent or derivative or fragment is defined as a molecule still having the same activity in transactivating the relevant genes from the relevant pathways (in kind, but not necessarily amount). Apart from being useful for biomass production and other uses of the micro-organisms themselves, another important use includes the production of recombinant proteins, homologous or heterologous. Thus the invention also provides methods for producing micro-organisms according to the invention, which micro-organisms further comprise a nucleic acid encoding such a protein of interest. Many proteins of interest have been disclosed and have been produced in yeast or other micro-organisms. They do not need to be reiterated here.

The micro-organisms produced by the methods according to the invention are also part of the invention. They are improved in many aspects, when compared with the organisms they are derived from, for instance they can have improved biomass yield upon culturing; they may show increased glucose oxidation; they may display increased oxidative sugar metabolism and/or reduced aerobic fermentation. Normally, under anaerobic culturing conditions the micro-organisms according to the invention will behave essentially the same as the corresponding micro-organism not provided with the modulation of this metabolic pathways.

The process to obtain the improved micro-organisms, in particular improved yeast has applications in all industrial processes in which optimal conversion of sugar into biomass is required. Use of these improved yeasts will lead to reduction of costs because of reduced process times and increased amounts of biomass per consumed glucose. This invention is well applicable in, for example, the (aerobic) production process of yeast for bakeries, or as source of flavour-enhancing yeast extracts. Furthermore this invention will lead to increased production of metabolites and heterologous gene products, such enzymes, precursors for chemicals, biosurfactants and fatty acids for application in pharmaceutical, agricultural or food sectors.

Concerning the application in baker's yeast or brewer's yeast, it should be noted that the reduction of alcohol formation in the production phase does not negatively affect growth or alcohol production during anaerobic fermentation, which is crucial for leavening of the dough or for the brewing process. This invention reduces alcohol production only when the yeast can make use of its enhanced respiratory capacity, i.e. under aerobic conditions.

The invention may also be applied with respect to manipulation of glucose repression or even glucose inactivation of processes not directly related to respiratory function of yeast. The uptake and metabolism of carbon sources other than glucose, such as galactose, sucrose or maltose is repressed by glucose. Yeast fermentation in lean dough depends on maltose as main substrate, which is produced in the dough from starch by action of amylases present in the flour. The flour contains in addition variable amounts of other sugars amongst which glucose. Maltose-permease, responsible for the translocation of maltose across the plasma membrane and maltase, the maltose metabolising enzyme, are both subject to glucose repression and inactivation (4).

Since this negatively affects $CO_2$ production and thereby leavening activity, tools to reduce the glucose effect on maltose uptake and utilisation would be useful. Therefore it is noteworthy this invention will even improve leavening activity of said yeast strains.

DETAILED DESCRIPTION

As stated before, a very important micro-organism is *Saccharomyces cerevisiae*. We will explain in detail how its reaction to the presence of glucose may be changed, as exemplary for other micro-organisms. In the presence of glucose Saccharomyces shows a "Crabtree" response and switches to ethanol production through aerobic fermentation.

The present invention in one embodiment offers a solution to such problems by the construction of production strains of micro-organisms in particular yeasts, more specifically *S. cerevisiae* in which the Crabtree-effect is reduced or absent. The principle of the approach is the controlled de-regulation of glucose-repressible genes by overexpression of a specific transcriptional activator from a promoter insensitive to glucose control. The resultant shift in balance from fermentative to oxidative metabolism leads to increased growth rates and reduced ethanol production.

Glucose Control of Metabolism in *S. cerevisiae*

The extensive changes in enzyme complement during a shift from oxidative/gluconeogenic to fermentative growth are, in the vast majority of cases, the result of induction or repression of transcription of the corresponding genes in response to glucose. Genes whose expression is repressed by this sugar can be divided into three groups:

1. Genes required for the uptake and metabolism of other carbon sources, such as galactose, sucrose, maltose, glycerol, lactate and ethanol.
2. Genes unique to gluconeogenesis and the glyoxylate cycle.
3. Genes coding for Krebs cycle enzymes and components of the respiratory chain.

Although each group displays distinct features of regulation, a number of common transcription factors and mechanisms are involved and these form the main glucose repression/deprepression pathway (MGRP; 2). As shown in FIG. 3, key events in this pathway are the activation or inhibition of a number of key transcription factors in response to a signal generated by glucose. The nature of this signal is unkown. Its main effect is, however, to inhibit or counteract the action of the Snf1/Snf4 complex, a protein serine/threonine kinase, which is thought to alleviate transcriptional repression and promote transcriptional activation at glucose-regulated promoters (5). Although as yet, there is no evidence that Snf1/Snf4 directly phosphorylates a transcriptional regulator, genetic studies suggest that important direct or indirect targets for Snf1/Snf4 are the transcription factor Mig1, Ssn6/Tup1 and Hap2/3/4. Mig1 is a zinc-finger protein which acts as a transcriptional repressor at many glucose-repressible genes (6) Ssn6/Tup1 acts as a repressor of transcription at a large number of genes, probably in combination with gene- or family-specific transcription factors (7). The Hap2/3/4 complex is, in contrast, an activator of transcription. It is required for induction of transcription by non-fermentable carbon sources of a limited number of genes encoding proteins involved mainly in mitochondrial electron transport, Krebs cycle, haem biosynthesis and gluconeogenesis (8, 9, 10, 11, 12). Transcriptional regulation by the Hap2/3/4 complex is the main mechanism for coordinating the derepression of these enzymes in response to changes in carbon status of the medium (11, 13). The activity of the Hap complex is controlled by the availability of the activator subunit Hap4, whose synthesis is approximately 5-fold repressed by glucose (13).

Transcription and Transcriptional Control in Yeast

A typical yeast promoter consists of several cis-acting elements that function as target sites for regulatory proteins (FIG. 2). The position of transcription initiation by the RNA polymerase II complex is located at the initiation site (I). The TATA-box (T) has been shown to be essential in many promoters for transcription initiation to occur. It is the target site for the basal RNA polymerase II transcription factor TFIID, which nucleates the assembly of the other basal transcription factors and RNA polymerase II into a stable preinitiation complex. In addition to these basal control elements, at least one upstream activation site (UAS) is required for transcription. UAS elements function as DNA binding sites for transcriptional regulatory proteins, that are thought to interact with the basal transcriptional machinery to mediate specific regulation. In many instances, yeast promoters consist of several TATA- and UAS-elements, which together determine the rate of transcription of the adjoining gene. In addition, yeast promoters may contain operators or upstream repressor sites (URS) and upstream induction sites (UIS). By binding of specific proteins these elements contribute to the overall transcriptional regulation.

Carbon Source-dependent Transcriptional Regulation by the Hap2/3/4 Complex

Carbon source dependent transcription of genes encoding a number of components of the mitochondrial respiratory chain and enzymes of gluconeogenesis is regulated by the Hap2/3/4 complex. Hap2 and Hap3 were first identified as proteins capable of binding to the UAS2 region of the gene encoding iso-1-cytochrome c in *S. cerevisiae* (14). This region, responsible for carbon source response, contains a sequence motif closely resembling the CCAAT box element found in many other eukaryotic promoters. The two proteins bind to DNA in an interdependent manner. Hap4 appears not to contact DNA directly, but is necessary for DNA binding of the other two proteins. Sequence analysis reveals a C-terminally located, highly acidic region whose presence is necessary for activity. Replacement of this region by the activation domain of the yeast Gal4 protein restores activity, suggesting that it provides the principal activation domain of the DNA-bound Hap2/Hap3 complex (13). Transcription of the genes for Hap2 and Hap3 in *S. cerevisiae* is not substantially affected by carbon source, but expression of the gene for Hap4 is glucose repressible (13). This suggests that Hap4 is the key component of the complex in terms of its ability to regulate transcriptional activity in response to carbon source.

Insight into the structure of the Hap2 and Hap3 proteins has been obtained by the isolation and sequencing of the corresponding genes. The HAP2 gene encodes a 265 residue protein, of which an evolutionarily-conserved 65 amino acid core in the highly basic C-terminal region is necessary and sufficient for both complex formation and binding to DNA (FIG. 4). The HAP3 gene encodes a 144 residue protein, which contains a 90 amino acid core (B-domain) required for complex formation and DNA-binding (FIG. 5). The HAP4 gene encodes a 554 residue protein containing two highly acidic regions in its C-terminal domain (13; FIG. 6). Both of these appear to be necessary for transcriptional activation.

Genes corresponding to HAP2 and HAP3 have been isolated from a wide range of organisms (15). The encoded proteins form a heteromeric complex called NF-Y, CBF or CP, which activates transcription by binding to the evolutionarily conserved CCAAT box element. Hap2- and Hap3-homologous subunits make similar contacts with DNA. For the human CP1 complex, it has been shown that the Hap2 and Hap3 homologues are exchangeable in vitro with those of yeast (16). However, although the human CP1 complex consists of more than two subunits, none of these appear to correspond to the *S. cerevisiae* Hap4 protein. The Hap homologous complexes are not specifically involved in induction of genes under certain growth conditions, but function as general transcription factors required for basal level expression of a large number of genes.

As the Hap complex (in the yeast *Saccharomyces cerevisiae*) is involved in the regulation of many metabolic processes, it is to be expected that modification of its expression has a. profound effect on the cell's physiology. With regard to anabolic processes, to date not much is known about its role but with regard to the catabolic network (that is, the energy conserving machinery) in *S. cerevisiae*, synthesis of components of the respiratory chain (hence mitochondrial) is to a significant extent under control of the Hap2/3/4 complex. It seems justified to conclude that Hap-dependent regulation is at least involved in the physiological phenomenon known as the Crabtree effect. Its direct physiological impact is a catabolic shift from respiratory to fermentative catabolism whenever elevated levels of glucose are present. This results in a significant decrease in the efficiency of energy conserved: only 2 moles of ATP are synthesized per glucose fermented to ethanol and carbon dioxide, whereas the number of moles of ATP (equivalents) per glucose oxidized (to carbon dioxide) is manyfold higher (the exact number still being a matter of debate). An important indirect effect is a decrease in anabolic capacity: it is known that the maximal obtainable growth rate of *S. cerevisiae* is highest under conditions that allow respiration. As a consequence, whenever conditions are such that the catabolic flux into respiration is increased, the yield value ($Y_{glucose}$, defined as the amount of cells obtained per glucose consumed) will be considerably higher and the organisms will grow faster. In other words, under such conditions the partitioning of the total carbon flux over the catabolic and the anabolic flux will be directed towards the latter. Thus, a larger part of the carbon source is directed towards biomass formation and a given biomass concentration is achieved in a reduced time span. Due to the said regulation (Crabtree effect), fully respiratory catabolism can only occur under aerobic conditions with continuously very low glucose availability, a condition not often met in practical settings.

According to the invention, the inhibition or circumvention of glucose-regulated partitioning of the catabolic fluxes should result both in increased Yglucose values and higher growth rates. Here, it is important to note that it can be foreseen that a relatively small increase in the respiratory flux may result in a significant gain in biomass yield due to the large difference in the energetic efficiency between respiration and fermentation. All anabolic processes will be enhanced and since anabolism comprises protein synthesis it is to be expected that said increase is beneficial not just to biomass production per se only but also to the production of specific proteins.

Modification of the expression of glucose repressed genes can be achieved by interference in other factors of the glucose repression signalling cascade besides Hap4. All mutations in upstream regulators of the cascade (see FIG. 3), like Snf1 or Hxk2, do alleviate glucose repression of SUC2, GAL, MAL and respiratory genes, but these mutants display a wide range of phenotypic defects (1, 17, 18) and are not suitable for industrial application of yeast. De-repression of SUC, MAL and GAL genes can also be accomplished by removal of the general glucose repressor Mig1, which results in partial alleviation of glucose control of maltose metabolism in a laboratory strain (19) This does however not affect glucose repression of respiratory genes, and no change in fermentative-oxidative metabolism, growth rate or cell mass yield.

We have now found that yeast, transformed with a construct that overexpresses the HAP4 gene, becomes insensitive to glucose repression of transcription of a number of genes, amongst which genes encoding respiratory components. This results in increased respiratory capacity of this yeast strain and reduced ethanol production. This altered aerobic sugar metabolism leads to a drastic increase in biomass yield and a significantly increased growth rate.

The present invention provides a transformed yeast with an reduced aerobic fermentation rate of glucose which comprises the introduction into yeast of a DNA construct which contains an homologous gene encoding a protein de-regulating glucose repression of a number of genes in the said yeast.

The homologous gene in this invention, HAP4 is cloned into a circular vector DNA construct which is transformed into yeast by a procedure described in the following section. The vector contains DNA sequences that enables replication in both *E. coli* and yeast, sequences that enable cloning of DNA fragments into the vector, a yeast marker gene and a bacterial marker gene that enables selective maintenance in yeast or *E. coli* respectively. After transformation of the vector into yeast, it will be self-replicating and be maintained as long as selective pressure against plasmid loss is sustained. During non-selective propagation (i.e. growth in the presence of leucine in this particular case), the plasmid will be lost. From a practical point of view, it is preferable to grow yeast non-selectively. This will entail alteration of expression of HAP4 by integration of the altered gene in the yeast chromosome. By "altered" is meant the exchange of the natural promoter by another promoter which is constitutively active, or by integration of a DNA construct consisting of such a promoter fused to the HAP4 gene on a different locus on the chromosome, e.g. the SIT2 locus (20). Integration of homologous yeast sequences is a well described and efficient technique (21) and can be easily applied to (industrial) yeast strains. The yeasts thus obtained are stable transformants and the altered HAP4 gene can be maintained in the genome without selective pressure.

Yeast with a chromosomally altered HAP4 gene can be constructed in such a way that the transformants are completely devoid of prokaryotic DNA, in contrast to the transformants also described in this invention which contain a plasmid harbouring prokaryotic DNA sequences. By integration of only homologous DNA, originating from Saccharomyces, one can improve the yeast without introducing any heterologous DNA.

The present invention comprises induction of changes in glucose metabolism by overexpression of a key transcriptional regulator of oxidative metabolism of yeast by introducing in the yeast a DNA construct expressing HAP4 under control of the ADH1 promoter, whose activity is enhanced approximately ten-fold by glucose. The elevated expression level has alternatively been achieved by using other strong promoters, which are constitutively expressed, independently of the presence of glucose. This is of particular importance for application in fed-batch cultures, where the glucose concentration is kept low in order to minimise the Crabtree-effect. Several promoters belonging to genes encoding enzymes of the glycolytic cycle, like glyceraldehyde-phoshate dehydrogenase (GPD) or genes involved in ribosomal expression, such as promoters for the transcription of elongation factors (EF) are well characterised and widely used for overexpression of yeast genes. These promoters have been isolated from *S. cerevisae* and cloned in expression vectors for yeast (22). The coding region of the isolated HAP4 gene was cloned behind these promoters, after which the promoter-HAP4 fusions were recloned in such a construct that the HAP4 gene with altered regulation of expression could be integrated into the yeast genome. This procedure leads to stable transformants which exhibit all the advantages described above due to more oxidative growth and which in addition do not contain any prokaryotic DNA sequences.

The yeast strains described in this invention comprise both laboratory strains and industrial production yeast strains. The overexpression of Hap4 was first achieved in a laboratory strain by means of introduction of a self-replicating plasmid harbouring the HAP4 gene under control of the ADH1 promoter. The metabolic behaviour of this engineered strain was tested in detail as described below, showing a significant increase in oxidative metabolism when grown on glucose. Industrial production strains were transformed with the same plasmid, which was slightly modified by introduction of a dominant marker thereby enabling selection of transformants containing the plasmid overproducing Hap4. The response of the industrial strains to Hap4 overexpression was similar to that of the laboratory strain, i.e. glucose repression of respiratory function is alleviated and therefore glucose metabolism has shifted from fermentative towards oxidative metabolism. To obtain stable yeast strains with all the advantages described above, genomic integration of constitutively expressed Hap4 was carried out, as described in detail in the following sections.

Experimental

*Saccharomyces cerevisiae* strain DL1 has been transformed with YCplac111::ADH1 (without any gene placed behind the ADH promoter) or YCplac111::ADH1-HAP4 (expression of HAP4 under control of ADH1 promoter). Transformation of the yeast strain with YCplac111::ADH1, the so-called "empty" plasmid is necessary to prevent any differences in physiology of the Hap4 overproducer and the wild type due to differences in e.g the plasmid encoded LEU2 marker gene. The nomenclature of the transformed yeast strains is as follows: DL1 denotes strain Dl1 transformed with YCplac111::ADH1, whereas DL1HAP denotes DL1 transformed with YCplac111::ADH1-HAP4. The expression level of HAP4 mRNA in these strains is depicted in FIG. 9. Expression of HAP4 in Dl1 is strongly repressed by glucose. Introduction of the plasmid with HAP4 under control of the ADH1 promoter leads to an increased expression level of HAP4 in DL1HAP which is grown on media containing 2% glucose. This level is comparable to the expression level of HAP4 in wildtype DL1 cells when grown on non-fermentable carbon-sources, which do not repress transcription of HAP4 and genes encoding respiratory components.

To study the effect of HAP4 overexpression on transcriptional control of respiratory function, we first studied the mRNA levels of different genes encoding components of the respiratory chain. As shown in FIG. 9, the elevated level of HAP4 in glucose containing medium leads to de-repression of transcription of QCR8, the gene encoding the 11 kDa subunit of the yeast ubiquinol-cytochrome c oxidoreductase (QCR) complex of the respiratory chain. Comparable results were obtained for a number of other genes encoding respiratory components (Table I). Transcription of SUC2, a glucose repressed gene without an Hap binding box in the promoter region is not induced by overexpression of HAP4 on glucose.

To test whether the increased level of mRNAs of respiratory components results in an higher respiratory capacity of the Hap4 overproducing strain, we measured oxygen consumption rates of cells as described in a previously section. Respiratory capacity of DL1HAP cells grown in shake flask cultures on complex media containing glucose is increased two-fold compared to wildtype cells (Table II). When grown in the presence of the non-fermentable carbon-source lactate, the respiratory capacity is further increased approximately five-fold to a level similar for both wildtype and Hap overproducing strains.

Further characterization of the physiological properties of the Hap4 overproducing strain required growth under controlled conditions (constant pH, aeration, stirring) in well defined mineral media (see section 'batch cultivation in fermentors'). Therefore, aerobic growth of Dl1 in a defined mineral salts medium containing 30 g/l (3%) glucose was compared with growth of Dl1HAP cells. As calculated from the growth curves (not shown), DL1 grew exponentially with a specific growth rate of $0.16\pm0.01$ $h^{-1}$, whereas the growth rate of DL1HAP was $0.18\pm0.01$ $h^{-1}$. Overproduction of Hap4 thus results in an increased growth rate of 11%.

During a period of six hours during exponential growth, samples were taken with an interval of one hour to measure substrate consumption and biomass and product formation. The mean biomass yield during this time course, i.e. the amount of biomass formed per gram consumed glucose is 10.1 gram for DL1 and 14.8 gram for DL1HAP. Overproduction of Hap4 thus leads to 46% increase in biomass yield compared to wild type, which is rather constant during the experiment (see FIG. 10).

Analysis of other carbon compounds present in the culture medium showed that ethanol production is significantly decreased (38%) in DL1HAP compared to the wild type (Table IV). The reduction in ethanol formation is accompanied by a 2.3-fold increase of the amount of acetate, whereas the amount of glycerol decreased 3.5-fold in DL1HAP cells. The oxygen consumption during the experiment was approximately twice as high in DL1HAP compared to DL1. All data are thus consistent with a shift of carbon metabolism from fermentative towards oxidative metabolism due to overexpression of HAP4. This is further illustrated in Table V, which summarizes carbon fluxes in both strains. The amount of $CO_2$ produced via TCA cycle was calculated by the amount of oxygen consumed during the experiment.

When grown under anaerobic conditions, both strains are identical with respect to growth rate, ethanol production and biomass yield (data not shown). This implies that overexpression of HAP4 only exhibits its effect during aerobic growth of yeast. Processes depending on anaerobic alcoholic fermentation, like brewing or dough leavening will be unaffected by HAP4 overexpression. This invention is therefore very well applicable in optimization of biomass yields in the aerobic production phase of industrial yeast strains.

Taking into account strain-dependent variations in glucose repression (23, 19), it should be mentioned that the regulation of expression of HAP4 in several industrial strains was found to be similar to laboratory strains described above and in literature (13), i.e. the expression is repressed by glucose (data not shown). To obtain constitutive high expression levels of HAP4 in the industrial strains, we integrated a DNA construct consisting of a constitutively active promoter (of glyceraldehyde-phosphate dehydrogenase, GPD1 and elongation factor 1-alpha, TEF2) fused to the coding region of the HAP4 gene in the genome of the yeast strain. The integration plasmid is constructed in such a way that the promoter-HAP4 fusion is flanked by DNA sequences representing parts of the yeast SIT2 gene (see FIGS. 11 and 13). Integration of the total plasmid including the promoter-HAP4 fusion can therefore take place at the SIT2 locus in the yeast genome. The presence of a gene encoding acetamidase (amdS) enables cells which have integrated the plasmid to grow on medium containing acetamide as a nitrogen source, in contrast to untransformed cells which are unable to grow on this medium. Since the plasmid does not contain any sequences which enable replication in yeast, integration of the plasmid in the genome is required to acquire the ability to grow on acetamide.

Strains DS28911, DS18332 and DS19806 were transformed with the plasmid pKSPO2-GPDHAP4 or pKSPO2-TEFHAP4. Transformants with an integrated plasmid in the genome were selected on plates containing acetamide. Transformants containing pKSPO2-GPDHAP4 were named DS28911GH, DS18332GH,or DS19806GH, transformants containing pKSPO2-TEFHAP4 DS28911TH, DS18332TH or DS19806TH. In a number of transformants the position of integration was analysed by Southern blotting, in which genomic DNA fragments containing SIT2 and/or HAP4 sequences were visualized (see FIG. 13). The length of the different fragments revealed that integration preferentially took place at the HAP4 locus, as shown in FIGS. 13 and 14. These (anaploid) transformants contain both one or more glucose repressed HAP4 genes and a HAP4 gene which is under control of a constitutively active promoter.

To test the expression level of HAP4 in these transformants, mRNA was analysed of cells grown aerobically in media containing 2% glucose. The mRNA expression level of one selected transformant of every strain containing either the GPDHAP4 (GH) or the TEFHAP4 (TH) is shown in FIG. 15. Different levels of HAP4 mRNA were obtained in the different strains and with the two different promoters. The effect of overexpression of HAP4 on expression of QCR8, a glucose-repressed gene encoding a subunit of the respiratory chain was analysed in four independent transformants. Strains exhibiting clear and reproducible de-repression of QCR8 were selected for further studies and are shown in FIG. 15. As a loading control a constitutively expressed gene (PDA, encoding a subunit of pyruvate dehydrogenase, (24)) was visualized, showing that the higher expression of QCR8 is due to HAP4 overexpression. The integrated constitutively expressed HAP4 thus appears to result in alleviation of transcriptional repression of a respiratory component, analogous to the effect of the plasmid encoded HAP4 under control of the ADH1 promoter as described above.

To test the respiratory capacity of DS28911, DS18332 and DS19806 with the integrated GPDHAP4 (GH) or the TEF- HAP4 (TH) fusion, we measured oxygen consumption rates of cells grown in medium containing 4% glucose. As shown in Table VI, overexpression of HAP4 on glucose results in an increase of he respiratory capacity, ranging from 2.2 to 4.1 fold the value found in the corresponding wild type cells. The respiratory capacity of cells grown in lactate containing medium is 7.7 fold higher than in wild type cells. The alleviation of glucose repression of respiratory function is thus only partial, but similar or even higher than obtained with the laboratory strain DL1 containing the ADH1-HAP4 fusion on plasmid. It can therefore be expected that the physiological advantages of the latter strain are also applicable to the industrial strains harbouring the integrated constitutively expressed HAP4.

Application of the modified industrial strains requires removal of any sequences that are not derived from yeast. The transformants contain the total plasmid pKSPO2-GPDHAP4 or pKSPO2-TEFHAP4 in the genome. The 'non-yeast', plasmid sequences can however be removed by homologous recombination of identical DNA segments in the genome, as depicted in FIG. 13. Cells which are devoid of plasmid sequences can be selected by growth on medium containing fluoro-acetamide, which is toxic for cells still containing the gene encoding acetamidase. When the plasmid is integrated at the HAP4 locus, this recombination event will cause loss of the GPD- or TEF-HAP fusion as well, resulting in a wild type strain. Only after integration at the SIT2 locus the chromosomal arrangement is such that recombination can also result in cells that still contain the GPD- or TEF-HAP4 fusion. These 'clean' transformants now only contain yeast sequences and are suitable for industrial application.

To obtain these clean transformants, strains DS28911, DS18332 and DS19806 were transformed with plasmid pKSPO2-GPDHAP4 or pKSPO2-TEFHAP4 which was linearized at the SfiI site (see FIG. 11B). This led to a higher efficiency of integration at the SIT2 locus, as shown by Southern blot analysis. Comparison of expected (FIG. 13) and obtained (FIG. 16A) DNA fragments of a number of transformants revealed a new set of strains overexpressing HAP4 from the SIT2 locus. The expression levels of HAP4, QCR8 and PDA1 were determined by northern blotting of mRNAs isolated from cells grown in medium containing 2% glucose. As shown in FIG. 17A, also in these strains the elevated expression of HAP4 resulted in alleviation of glucose repression of QCR8. Subsequently we selected fluoro-acetamide resistant cells that had lost their plasmid sequences (including the acetamidase gene) by homologous recombination. Transformants which retained the GPD- or TEF-HAP4 fusion in the genome were selected by verification of the correct chromosomal arrangement by Southern blot analysis. FIG. 16B shows three examples of clean transformants derived from transformants DS18332GH15 and DS18332TH25. As shown in FIG. 17B, removal of the plasmid sequences has no negative effect on either HAP4 overexpression or QCR8 derepression. The effect of the HAP4 overexpression in these strains on oxidative metabolism can therefore be expected to be similar to those described above.

EXPERIMENTAL PROCEDURES

Cloning Techniques

All general cloning techniques (plasmid isolation, restriction, gel electrophoresis, ligation) were carried out as described by Maniatis et. al., Molecular Cloning, A Laboratory manual, Cold Spring Harbor Laboratory, Cold Spring Harbor, N.Y. (1982). DNA restriction enzymes were purchased from New England Biolabs (Biolabs), Boehringer Mannheim (Boehringer) or Bethesda Reseach laboratories (BRL). These enzymes were used in conditions and buffers described by the manufacturer.

Construction of Recombinant Plasmid YCplac111::ADH1-HAP4

The centromeric plasmids YCplac111::ADH1 and YCplac111::ADH1-HAP4 are capable of self-replicating in E. coli and in yeast and contains the ADH1 promoter region without (YCplac111::ADH1) or with the coding sequence of HAP4. The construction of YCplac111::ADH1-HAP4 is outlined in FIG. 7.

YCplac111::ADH1 is derived from YCplac111 (25) and contains between the BamHI and the SmaI site a 723 bp EcoRV promoter fragment from pBPH1 (26). Vector pBPH1 was derived from pAC1 (27), which is a YCp50 derivative which carries the BamHI/HindIII fragment from pMAC561 containing the yeast alcohol dehydrogenase I promoter (28).

The coding region of HAP4 was cloned behind the ADH1 promoter in the former construct by isolation of HAP4 from pSLF406 (13). pSLF406 was digested with BspHI, which cleaves HAP4 at position −1 relative to the start codon the coding sequence. The BspHI end was blunted and subsequently the HAP4 fragment obtained by cleavage of the DNA with PstI and isolation from agarose gel. YCPlac111 was cleaved with SmaI and PstI and ligated with the HAP4 fragment to generate YCplac111::ADH1-HAP4.

Construction of Recombinant Integration Plasmids p425-GPDHAP4, p425-TEFHAP4, pKSPO2-GPDHAP4 and pKSPO2-TEFHAP4

The plasmid pKSPO2 is used for integration of a fusion of HAP4 and the GPD1 or TEF2 promoter. These fusions were first constructed in shuttle vectors containing either the GPD1 (p425GPD) or the TEF2 promoter region (p425TEF) (22). A 2621 bp fragment from pSLF406 (13), containing the HAP4 gene, was isolated after digestion with BspHI, blunting and digestion with PstI as described in the previous paragraph. This HAP4 fragment was cloned in SmaI and PstI sites of the vectors 425GPD or p425TEF, resulting in the vectors p425-GPDHAP4 and p425-TEFHAP4 respectively. These shuttle vectors can self-replicate in E. coli and in yeast, but will only be maintained in yeast when selective pressure is present, i.e. when the recipient strain is LEU2 auxotrophic. In industrial strains without auxotrophic markers, integration of the GPDHAP or TEFHAP fusion is required to maintain the altered HAP gene stable in yeast. The promoter-HAP4 fragments were therefore recloned into the integration vector pKSPO2 (constructed at and provided by Gistbrocades). A 3359 bp Ecl136II-SalI GPDHAP4 fragment was isolated from p425-GPDHAP4 and a 3081 bp Ecl136II-SalI fragment was isolated from p425-TEFHAP4, which were cloned into pKSPO2 digested with SmaI and SalI. The different cloning steps are schematically drawn in FIG. 11. FIG. 12 shows the DNA sequence of the GPDHAP4 and TEFHAP4 fusions.

Transformation Procedures

Transformation of E. coli was carried out using the electroporation technique, using a Biorad E. coli pulser according to the description of the manufacturer.

Yeast cells were transformed according to the LiAc method described by Ito et al (29). Transformants of strain DL1 with the plasmid YCplac111::ADH1-HAP4 were selected on plates containing 2% glucose, 2% agar, 0.67% Yeast Nitrogen Base (Difco) supplied with the required aminoacids but lacking leucine. The industrial strains DS28911, DS18332 and DS19806 were plated on medium consisting of 1.8% nitrogen-free agar (Oxoid), 1.17% Yeast Carbon Base (Difco), 30 mM phosphte buffer pH 6.8 and 5 mM acetamide (Sigma).

Counterselection of Transformants

To select for transformants which after integration of the plasmid pKSPO2-GPDHAP4 or pKSPO2-TEFHAP4 recombine the plasmid sequences out of the genome (see FIG. 13), counterselection was carried out on plates containing 1.8% nitrogen-free agar, 1.17% Yeast Carbon Base, 30 mM phosphate buffer, 60 mM fluoro-acetamide (Fluka) and 0.1% $(NH_4)_2SO_4$. Transformants were grown in YPD medium for 60 to 70 generations by daily dilution of the cultures for 3 to 4 days. Aliqouts of the cultures were plated on the fluoro-acetamide containing plates, which selects for cells which have recombined out the acetamidase gene. The presence of the GPDHAP4 or TEFHAP4 fusion was tested by Southern blot analysis.

Growth of Yeast in Flask-batch Cultures

For shake flask cultivation, yeast cells were grown in either YPD (1% Yeast Extract, 1% BactoPeptone, 3% D-Glucose), YPEG (Yeast Extract , 1% BactoPeptone, 2% Ethanol, 2% Glycerol), YPL (lactate medium: 1.5% lactic acid, 2% Na-lactate, 0.1% Glucose, 8 mM MgSO4, 45 mM $(NH)_2HPO_4$, 0.5% Yeast-extract) or in mineral medium (0.67% Yeast Nitrogen Base) containing 3% D-glucose and supplemented with the appropiate aminoacids to obtain selective pressure for maintenaince of the transformed plasmid.

All cultures were inoculated from precultures which were prepared by inoculation of 5 ml medium with a colony from a plate. For northern analysis and oxygen consumption capacity measurements, the wild type and modified industrial yeast strains were precultured overnight in YPD and strain DL1 containing YCplac111::ADH1-HAP4 and Dl1 containing the empty YCplac111 vector were precultured overnight in mineral medium with additional amino acids. These cultures were used to inoculate 100 ml YPEG and/or YPD medium and grown overnight at 28° C. to $OD_{600}$~1.5, after which cells were harvested by centrifugation.

Growth of Yeast in Fermentor-batch Cultures

Transformed yeast cells were grown in selective mineral Evans medium containing 30 g $l^{-1}$ D-Glucose and supplemented with 40 mg $l^{-1}$ uracil and L-histidine. The mineral medium contained: $NaH_2PO_4.2H_2O$, 10 mM; KCl, 10 mM; $MgCl_2.6H_2O$, 1.25 mM; $NH_4Cl$, 0.1 mM; $Na_2SO_4$, 2 mM; $C_6H_9NO_6$, 2 mM; $CaCl_2$, 20 mM; ZnO, 25.3 mM; $FeCl_3.H_2O$, 99.9 mM; $MnCl_2$, 50.5 mM; $CuCl_2$, 5 mM; $CoCl_2$, 10 mM; $H_3BO_3$, 5.2 mM; $Na_2MoO_4.2H_2O$, 0.08 mM. After heat sterilization of the medium at 120° C., filter sterilized vitamins were added to final concentrations per liter of myoinositol, 0.55 mM; nicotineacid, 0.16 mM; Ca-D(+)panthothenate, 0.02 mM; pyridoxine-HCL, 0.013 mM; thiamine-HCl, 0.006 mM; biotin, 0.02 mM. Cultivation was performed at 28° C. in New Brunswick Scientific Bioflow fermentors, at a stirrer speed of 900 rpm. The pH was kept constant at pH5.0 via the automatic addition of 2 mol $l^{-1}$ NaOH. Antifoam (BDH) was added automatically at fixed time intervals. The fermentors were flushed with air at a flow rate of 0.8 I $min^{-1}$. The starting working volume of the cultures was 1.0 or 1.4 liter. Samples of 30 ml were taken every hour for analysis of culture purity, dry weight, substrate consumption and product formation.

Determination of Culture Optical Density and Dry Weight

Optical cell density of cultures was measured in a spectrophotometer at 600nm. The dry weight of cultures was determined by centrifugation of 10.0 ml of culture, washing cells with demineralized $H_2O$, and drying the cellpellet overnight at 80° C. Parallel samples varied by less than 1%.

Substrate Consumption and Product Formation in Liquid Medium

Concentrations of carbon compounds, like glucose, ethanol, glycerol, acetate and pyruvate were determined by HPLC analysis using an Aminex HPX87H organic acids column of Biorad at 65° C. The column was eluted with 5 mM $H_2SO_4$. Detection was by means of a 2142 refractive index detector (LKB) and SP4270 integrator of Spectra-Physics.

Analysis of $CO_2$ Production and $O_2$ Consumption

During cultivation in fermentors, the dissolved carbondioxide concentration was continuously monitored by a cervomex IR PA404 gas analyzer and oxygen by a Taylor cervomex OA 272 gas analyzer. The absolute amounts of gas consumption/production during the time course of the experiment was calculated by the mean of the gas concentration, corrected for the decreasing volume of the culture.

For oxygen consumption capacity measurements of flask-batch grown cells, the cells were harvested, washed three times with ice-cold demineralized $H_2O$, and resuspended in oxygraph buffer (1% Yeast Extract, 0.1% $KH_2PO_4$, 0.12% $(NH4)_2SO_4$, pH 4.5) at 200 OD units $ml^{-1}$. Oxygen consumption capacity of the cells was measured with a Clark electrode, with 0.1 mM ethanol as substrate.

RNA Isolation, Northern Analysis and Labelling of DNA Fragments

Cells were harvested and RNA was isolated, separated on a non-denaturing 1.2% agarose gel and transferred to a nitrocellulose filter as described by De Winde (30). Prehybridization was performed in hybridization buffer containing 50 microgram/ml single stranded salm sperm DNA (50% formamide, 25 mM NaPi pH 6.5, 5×SSc, 5×Denhardt, as described by Maniatis (31). DNA fragments used as probes in this study include a 840 bp HindIII-SalI fragment from pJH1 (30); a 1.6 kb BamHI-KpnI fragment containing the yeast actin gene (24); a 2.5 kb HindIII-SalI fragment from YE23SH containing the QCR2 gene (25); a 1333 bp NcoI-HindIII fragment from pAZ6 containing the yeast PDA1 gene (24) and a 1.2 kb BamHI-HindIII fragment from YE23R-SOD/SUC containing the SUC2 gene (26). Fragments were labeled $^{32}p$ by nicktranslation as described by Maniatis et al. Labeled probes were added to the prehybridization buffer and hybridization was performed overnight at 42° C. Blots were washed once with 2×SSC 0.1% SDS, twice with 1×SSC, 0.1% SDS and finally with 0.5×SSC, 0.1% SDS. Blots were air-dried completely and autoradiography was performed with Kodak Xomat 100 film or analysed by a Storm 840 Molecular Dynamics Phosphorimager.

Chromosomal DNA Isolation and Southern Blotting

Chromosomal DNA was isolated according to the method described by Hoffman and Winston (34). 10 microliter of the chromosomal DNA was digested with either BamHI or EcoRI. The digested DNA was separated on a 1% agarose gel and transferred to nitrocellulose filter as described in Maniatis (31) Prehybridization of the filters was performed at 65° C. in 6×SSC, 5×Denhardt, 0.5% SDS and 100 microgram/ml salmon sperm DNA. After 4 hours prehybridization, a radioactive labeled KpnI-XbaI fragment from pKSPO2-GPDHAP (see FIGS. 11B and 13) was added and hybridization was continued overnight at 65° C. Blots were washed once with 2×SSC 0.1% SDS, twice with 1×SSC, 0.1% SDS and finally with 0.5×SSC, 0.1% SDS. Blots were air-dried completely and radioactivity was visualised and analysed by a Storm 840 Molecular Dynamics Phosphorimager.

DESCRIPTION OF THE FIGURES

FIG. 4. Nucleotide and amino-acid sequence of the HAP2 gene (SEQ ID NO:1).

FIG. 5. Nucleotide and amino-acid sequence of the HAP3 gene (SEQ ID NO:3).

FIG. 6. Nucleotide and amino-acid sequence of the HAP4 gene (SEQ ID NO:5).

FIG. 8. Nucleotide and amino-acid sequence of the ADH1-HAP4 fusion (SEQ ID NO:7).

FIGS. 12. 12A. Nucleotide and amino acid sequence of the GPD1 promoter fused to the coding region of HAP4 (SEQ ID NO:8). 12B. Nucleotide and amino acid sequence of the TEF2 promoter fused to the coding region of HAP4 (SEQ ID NO:9). The fragments shown are the fragments as cloned into pKSPO2 and represent the sequence as integrated in the genome FIG. 13. Scheme of genomic DNA at HAP4 and SIT locus and chromosomal rearrangements after integration of the plasmid pKSPO2-GPD1 or pKSPO2-TEFHAP4 on either the SIT2 locus or the HAP4 locus, and after counterselection on fluoro-acetamide (Fac). Fragments generated after digestion with BamHI or EcoRI which hybridize with the KpnI-XbaI probe (shown as thick black bar) are visualized for comparison with the Southern blots shown in FIGS. 13 and 15. SITpr: SIT2 promoter, HAP4pr: HAP4 promoter, G/Tpr: GPD or TEF promoter, B: BamHI, E: EcoRI, K: KpnI, X: XbaI, FacR: fluoro-acetamide resistant.

FIGS. 17A. and 17B. Northern blot of total mRNA of transformants with pKSPO2-GPDHAP (GE) or pKSPO2-TEFHAP (TH) integrated at the SIT2 locus as in FIG. 16. The blots were hybridized with probes specific for HAP4, QCR8 or PDA1 mRNA.

REFERENCES

Figure 1:
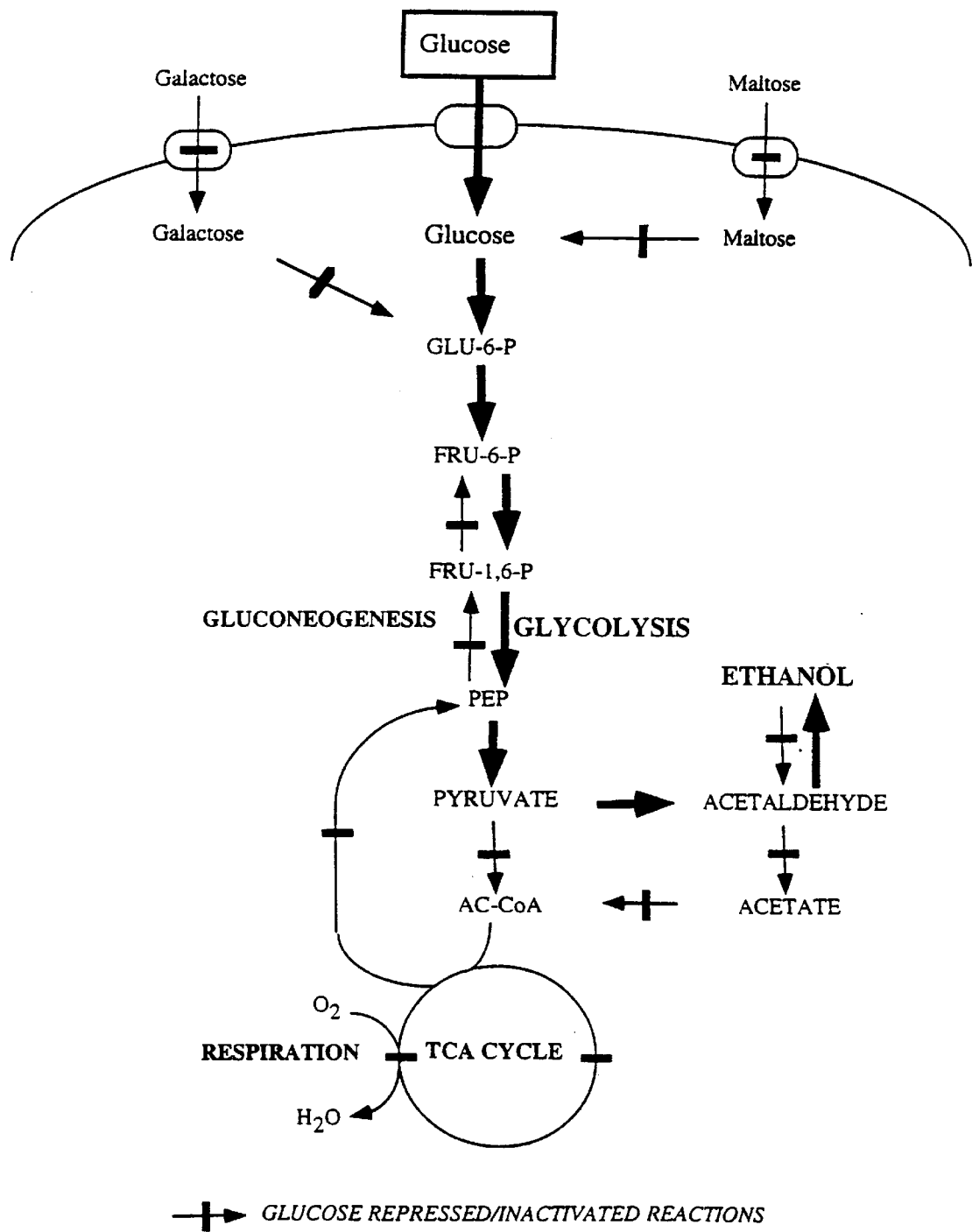
FIG. 1. Simplified view of the carbon metabolism in glucose-repressed *Saccharomyces cerevisiae* cells. Only a number of intermediates are shown, and specific pathways for the utilization of other carbon sources than glucose are only shown for maltose and galactose.
Figure 2:
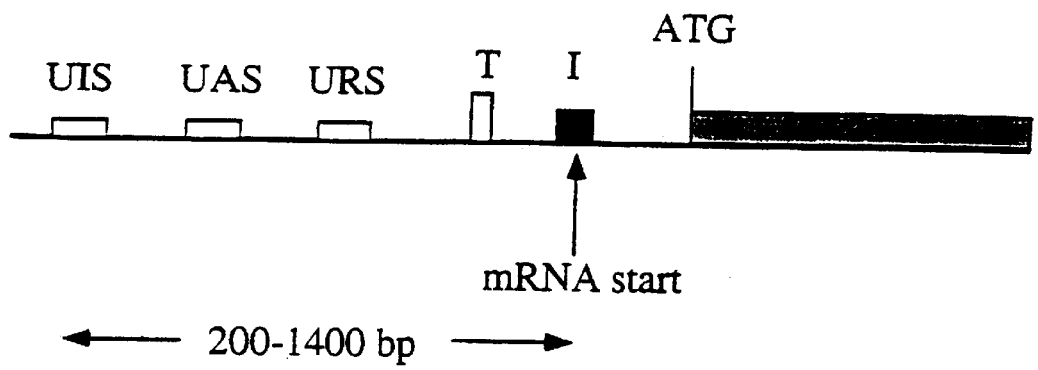
FIG. 2. Transcriptional regulation of a typical yeast promoter. ATG denotes the start codon of the corresponding translational open reading frame. Abbreviations: UIS, upstream induction site; UAS, upstream activation site; URS, upstream repressor site; T, TATA-box, I, initiation site.
Figure 3:
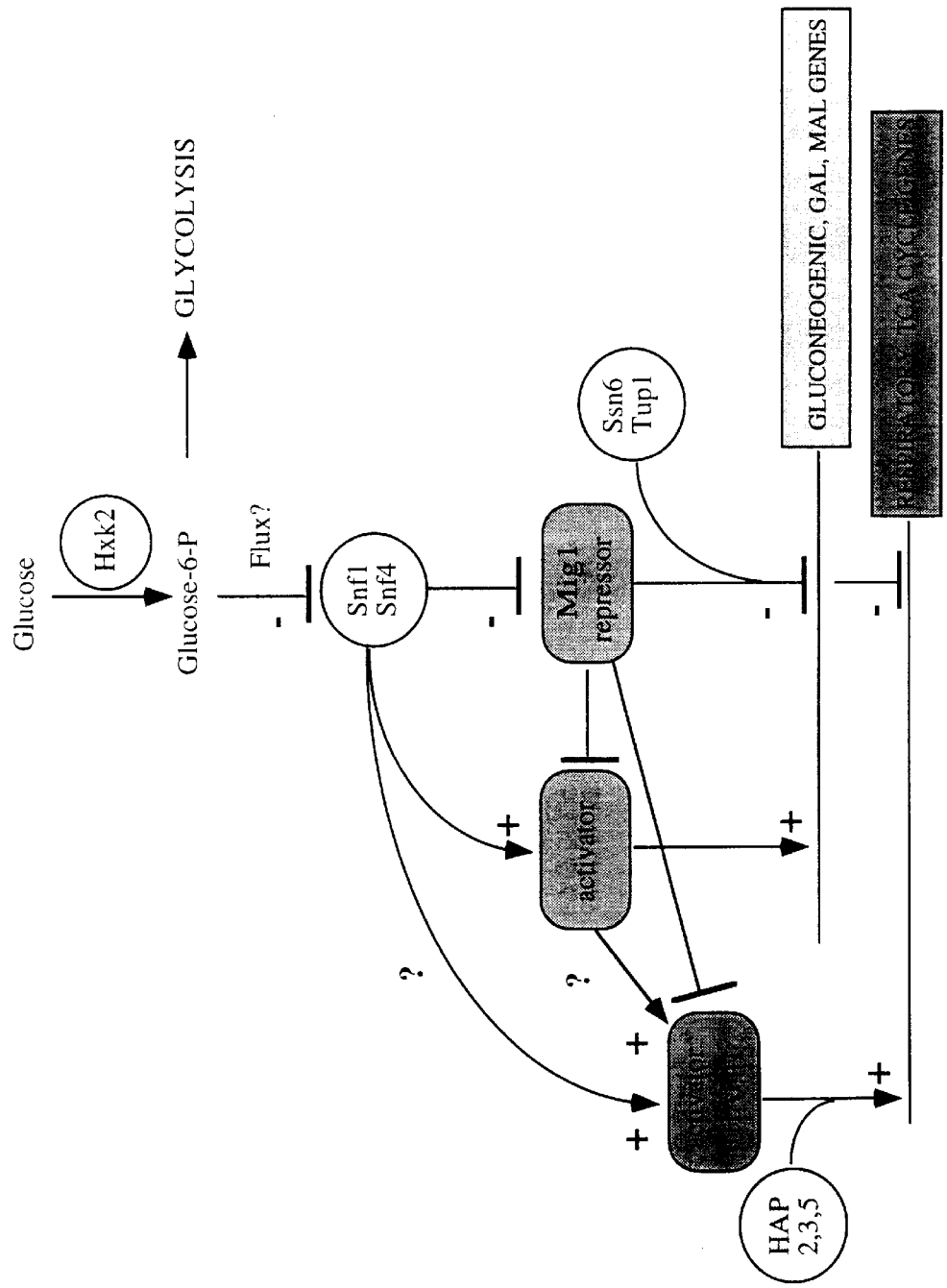
FIG. 3. Schematic representation of the regulatory pathways involved in glucose repression of a number of genes in yeast. Activating functions are denoted as (+), repressing/inactivating functions as (−), and interactions which are not resolved yet are denoted as (?).
Figure 7:
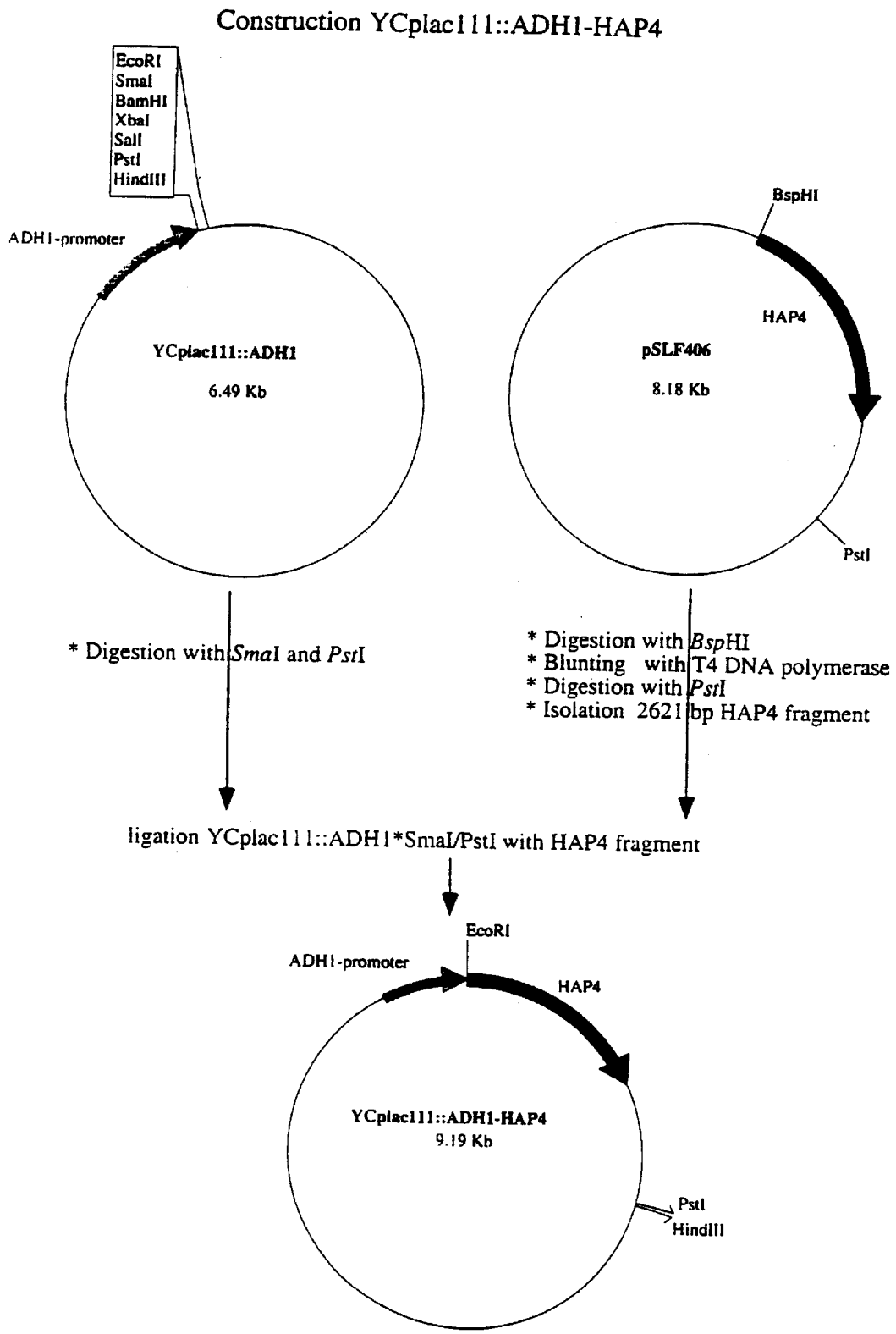
FIG. 7. Illustrates the construction of YCplac111::ADH1-HAP4, a yeast shuttle vector where HAP4 is expressed from the ADH1 promoter. Plasmids are not drawn to scale.
Figure 9:
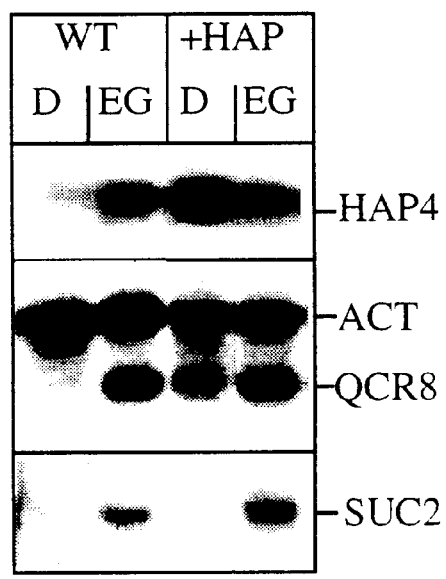
FIG. 9. Northern blot analysis of HAP4 overexpression. Dl1 containing YCplac111ADH1 (WT) and DL1 containing YCplac111::ADH1-HAP4 (+HAP4) were grown in medium containing 2% glucose (D) or 2% ethanol/2% glycerol (EG). Total RNA was hybridized with probes specific for HAP4, actin (ACT), QCR8, or SUC2 mRNA.
Figure 10:
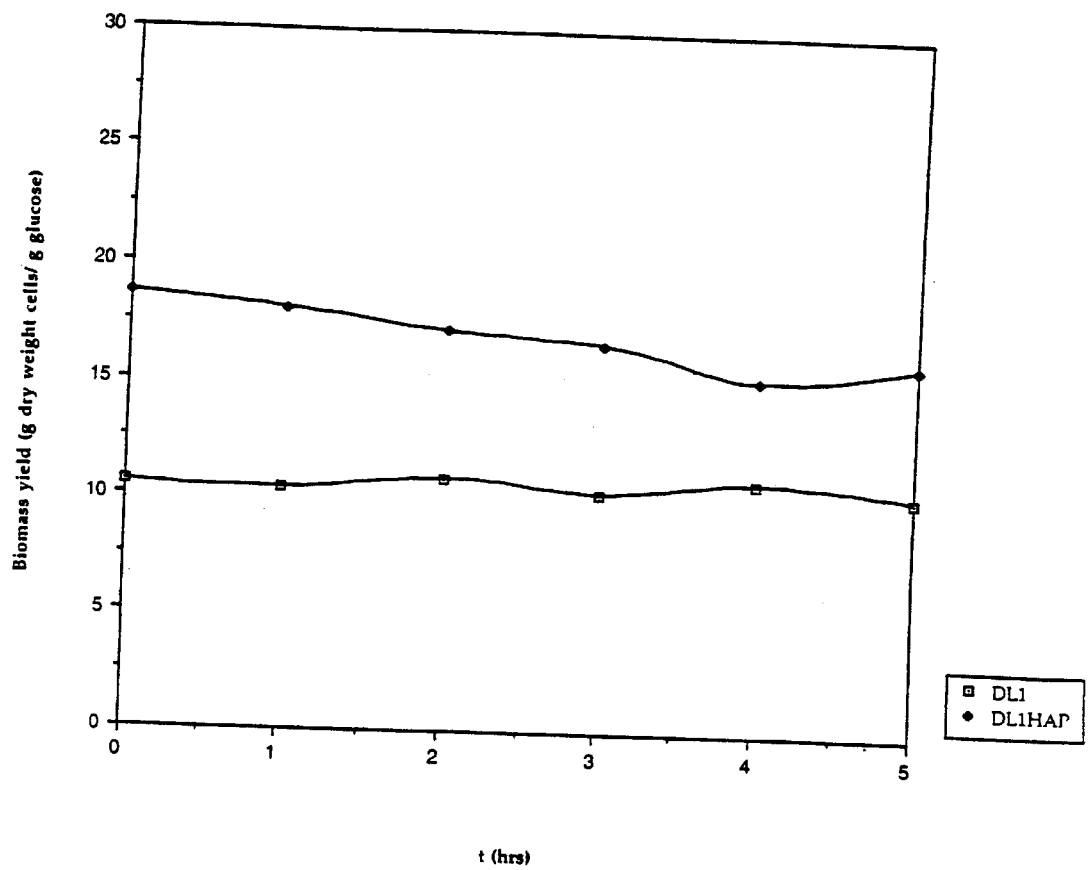
FIG. 10. Biomass yield. Dl1 containing YCplac111::ADH1 (DL1) and DL1 containing YCplac111::ADH1-HAP4 (DL1HAP) were grown in fermentors. Samples for determination of dry weight and glucose concentration were taken with an interval of one hour.
Figure 11A:
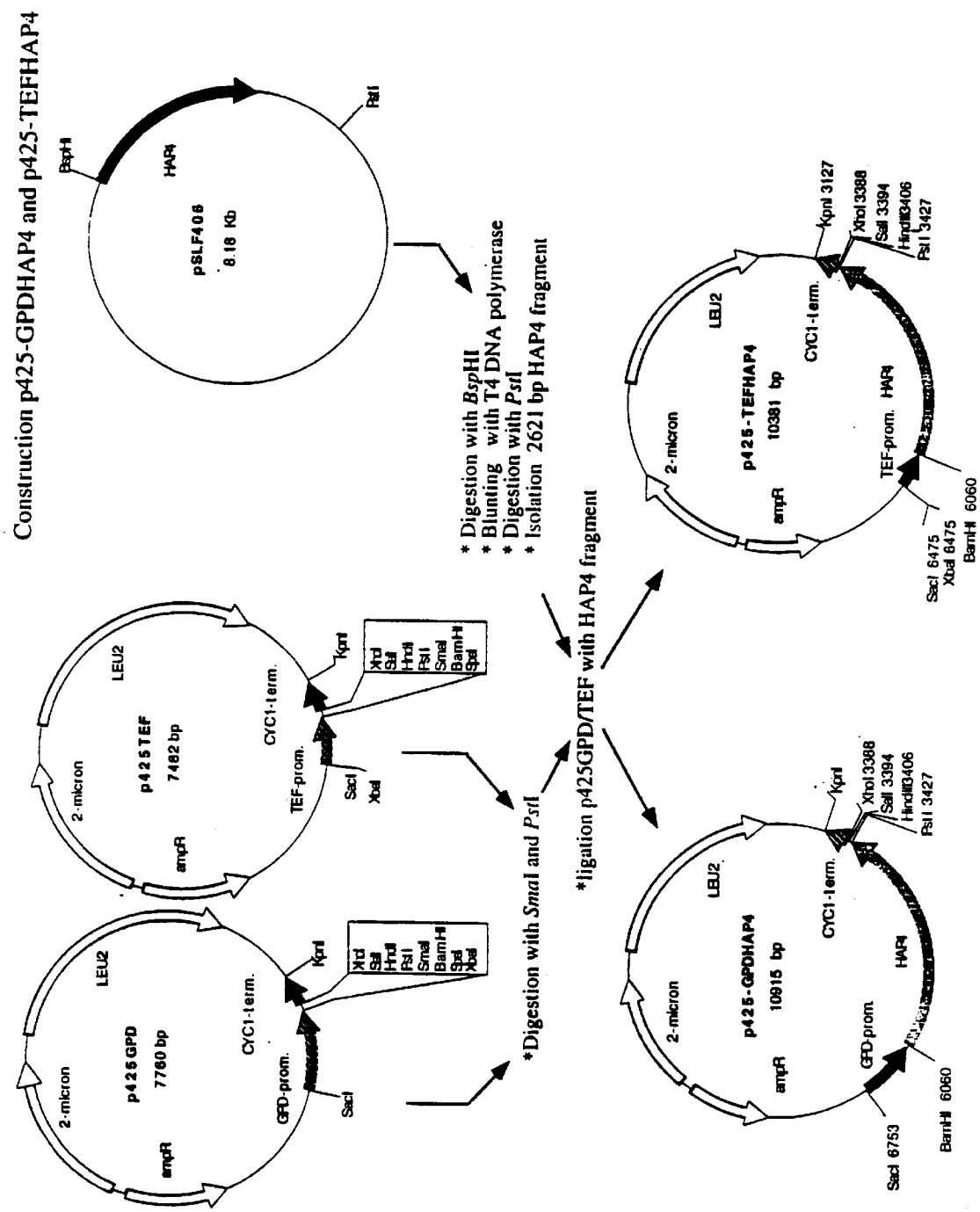
FIGS. 11. 11A. Construction of the plasmids p425-GPDHAP4, p425-TEFHAP4, 11B. Construction of the plasmids pKSPO2-GPDHAP4 and pKSPO2-TEFHAP4
Figure 13:
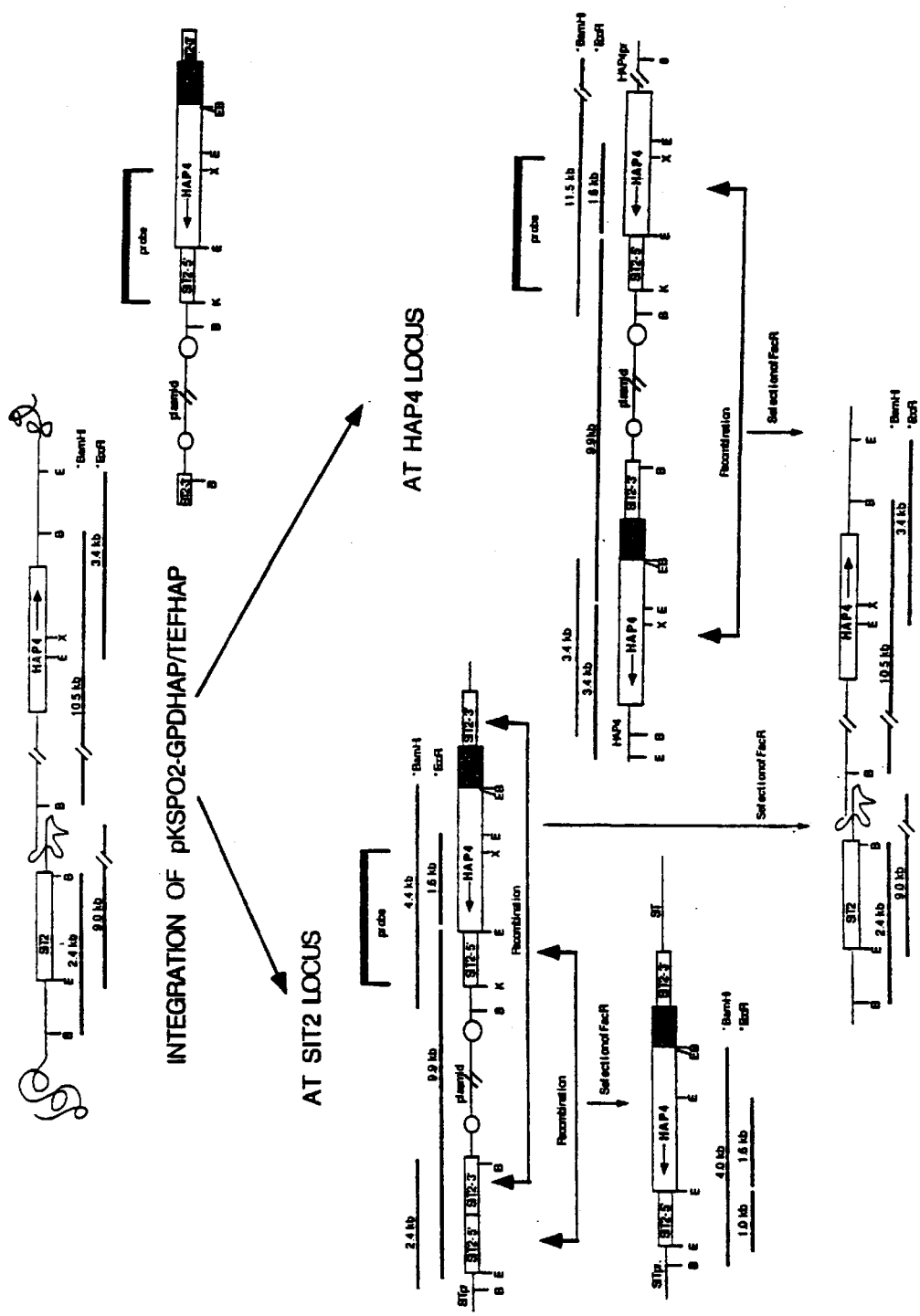
Figure 14:
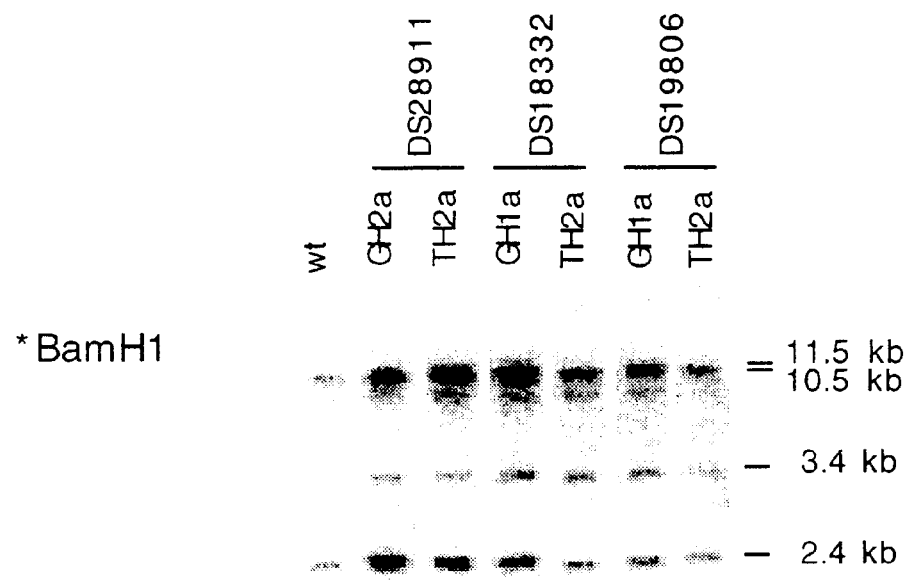
FIG. 14. Southern blot of chromosomal DNA digested with BamHI of transformants with pKSPO2-GPDHAP (GH) or pKSPO2-TEFHAP (TH) integrated at the HAP4 locus. The blot was hybridized with the KpnI-XbaI probe shown in FIG. 12, visualizing fragments containing SIT2 and/or HAP4 sequences. Radioactivity was visualised and analysed by a Storm 840 Molecular Dynamics Phosphorimager.
Figure 15:
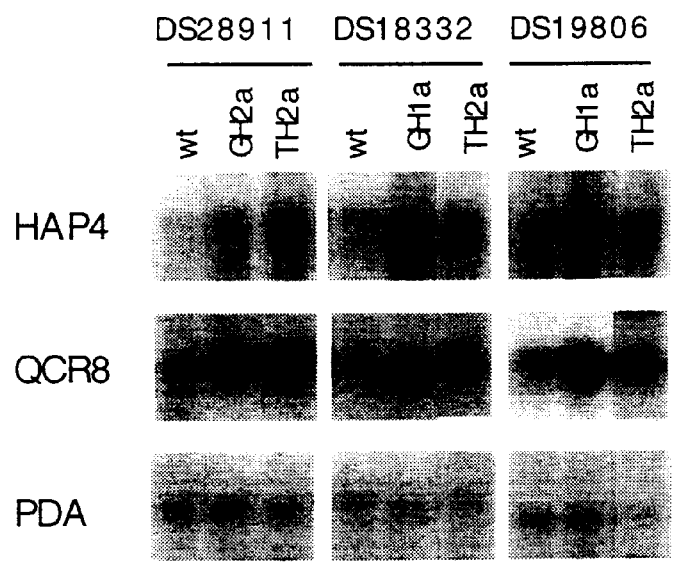
FIG. 15. Northern blot of total mRNA of transformants with pKSPO2-GPDHAP (GH) or pKSPO2-TEFHAP (TH) integrated at the HAP4 locus as in FIG. 14. The blots were hybridized with probes specific for HAP4, QCR8 or PDA1.
Figure 16:
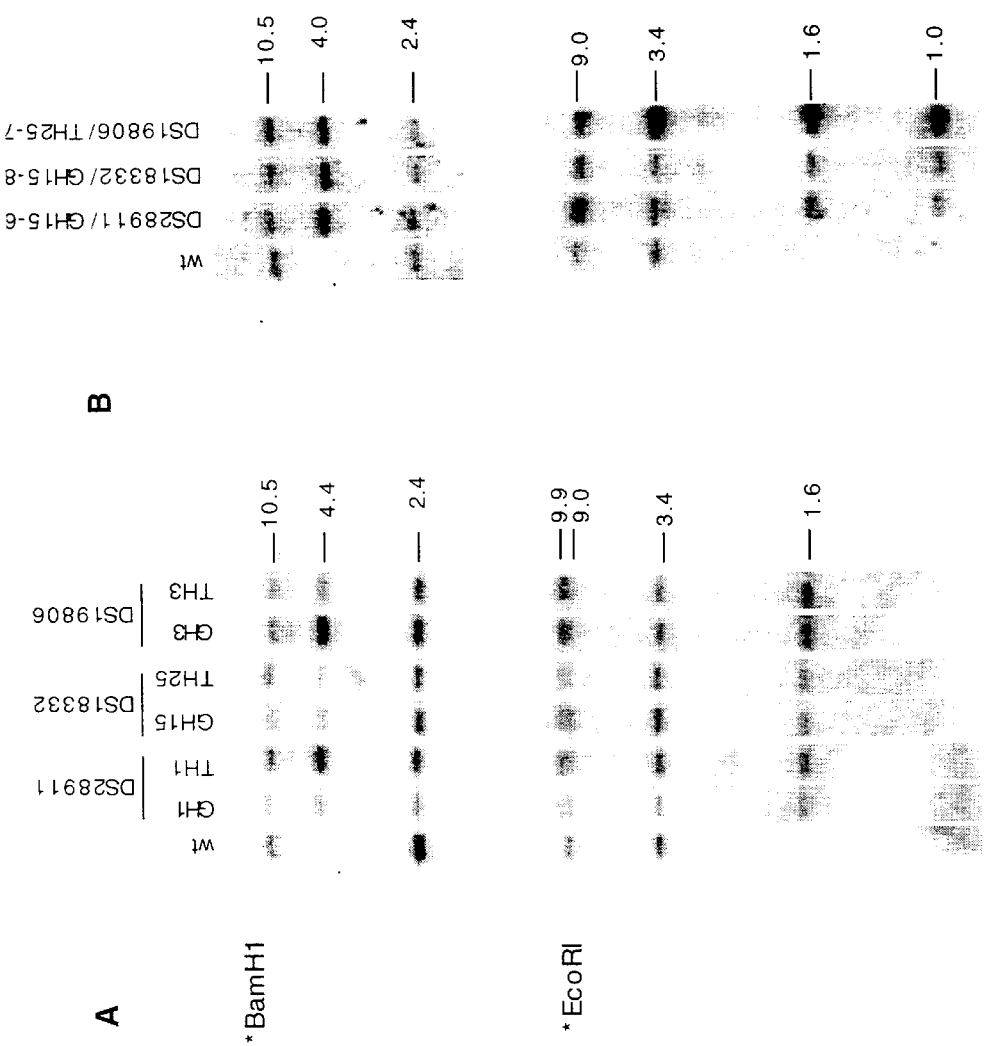
FIGS. 16A and 16B. Southern blot of chromosomal DNA digested with BamHI or EcoRI of transformants containing pKSPO2-GPDHAP (GH) or pKSPO2-TEFHAP (TH) integrated at the SIT2 locus 16(A) and three clean transformants containing the GPDHAP4 or TEFHAP4 fusion after counterselection on fluoro-acetamide 16(B). The blot was hybridized with the KpnI-XbaI probe shown in FIG. 12, visualizing fragments containing SIT2 and/or HAP4 sequences.

1. Ronne, H: Glucose repression in fungi. (1995) Trends in Genet. 11: p. 12
2. Thevelein, J. M., Hohmann, S.(1995) Trends in Biochem. Sci. 20: p. 3
3. Sierkstra, L. N., Nouwen, N. P., Verbakel, J. M. A., Verrips, C. T. (1993) Yeast 9: p. 787
4. Needleman, R. B., Kaback, D. B., Dubin, R. A., Perkins, E. L., Rosenberg, N. G., Sutherland, K. A., Forrest, D. B., Michels, C. A. (1984) Proc. Natl. Acad. Sci. USA 81, p2811
5. Lesage, P., Yand, X., Carlson, M.(1996) Molec. Cell. Biol. 16: p. 1921
6. Nehlin, J. O. and Ronne, H. (1990) EMBO J. 9: p. 2891
7. Treitel, M. A., Carlson, M. (1995) Proc. Natl. Acad. Sci., USA 92: p. 3132
8. Guarente, L., Lalonde, B., Gifford, P., Alani, E.(1984) Cell , 36: p. 503
9. de Winde, J. H., Grivell, L. A., ed. Global regulation of mitochondrial biogenesis in Saccaromyces cerevisiae. Progr. in Nucl. Acid Res. Mol. Biol., ed. Cohn, W. E., Moldave, K. Vol. 46. 1993, Academic Press: San Diego. p. 51
10. Dang, V. D., Valens, M., Bolotin-Fukuhara, M., Daignan-Fornier, B. (1994). Yeast 10: p. 1273
11. Bowman, S. B., Zaman, Z., Collinson, L. P., Brown, A. J. P., Dawes, I. W. (1992) Mol. Gen. Genet. 231: p. 296
12. Rozenkrantz, M., Kell, C. S., Pennel, E. A., Devenish, L. J. (1994) Mol. Microbiol. 13: p. 11913.
13. Forsburg, S., Guarente, L. (1989) Genes and Dev. 3: p. 1166
14. Olesen, J., Hahn, S., Guarente, L.(1987) Cell SI: p. 953
15. Li, X. Y., Mantovani, R., Hooft van Huijsduijnen, R., Andre, I., Benoist, C., Mathis, D.(1992) Nucl. Acids Res. 20: p. 1087
16. Sinha, S., Maity, S. N., Lu, J., de Crombrugghe, B.(1995) Proc. Natl. Acad. Sci., USA, 92: p. 1624
17. Johnston, M. and Carlson, M. (1992) In Jones, J., Pringle, J. R., Broach, J. R. (ed.) The molecular and cellular biology of the yeast Saccharomyces: gene expression. Cold. Spring Harbor Laboratory Press, Cold Spring Harbor, N.Y., p. 220–237
18. Trumbly, R. J. (1992) Molec. Microbiol. 6: p. 15
19. Klein, C. J. L., Olsson, L., Ronnow, B., Mikkelsen, J. D., Nielsen, J. (1996) Applied and Environmental Microbiology 62: p 4441

20. Gottlin-Ninga, E., Kaback, D. B. (1986) Mol. Cell. Biol. 6: p. 2185
21. Rothstein, R. J. (1983) Methods in Enzymology 101, p202
22. Mümberg, D., Muller, R., Funk, M. (1995) Gene 156: p. 119
23. Brown, T. A., Trumpower, B. L. (1995) J. Bact. 177: p. 1380
24. Wenzel, T. J., Zuurmond, A.-M., Bergmans, A., van den Berg, J. A., Steensma, H. Y. (1994) Yeast 10: p. 297
25. Gietz, R. D. & Sugino,A. (1988) Gene 74: p. 527
26. van Loon, A. P. G. M., Brändli, A. W., Pesold-Hurt, B., Blank, D., Schatz, G. (1987) EMBO J. 6: p. 2433
27. Hurt, E. C., Müller, U., Schatz, G. (1985) EMBO J. 4: p. 3509
28. Mc Knight, G. L. and McConaughy, B. L. (1983) Proc. Natl. Acad. Sci. USA 80: p. 4412
29. H. Ito, Y. Fukuda, M. Murata, A. Kimura (1983), J. Bact. 153: p. 163
30. De Winde, J. H. and Grivell, L. A.(1992) Mol.Cell. Biol 12: p. 2872.
31. Maniatis et. al.(1982) Molecular Cloning, A Laboratory manual, Cold Spring Harbor Laboratory Press, Cold Spring Harbor, N.Y., p 9.49–9.52)
32. Ng, R. and Abelson, J. (1980) Proc. Natl. Acad. Sci. USA 77: p. 3912
33. Oudshoorn, P., van Steeg, H., Swinkels, B., Schoppink, P., Grivell, L. A. (1987) Eur.J. Biochem. 163: p. 97
34. van Steeg, H., Oudshoorn, P., van Hell, B., Polman, J. E. M., Grivell, L. A. (1986) EMBO J. 5: p. 3643
35. Hoffman, C. S., Winston, F. (1987) Gene 57: p. 267

TABLE I

Effect of induced expression of HAP4 on transcription

| gene | protein | functional HAP 4 binding site | expression in wildtype on glucose | expression in HAP 4 - overproducer on glucose |
|---|---|---|---|---|
| QCR8 | 11 kD subunit VIII | + | repressed | induced |
| QCR7 | 14 kD subunit VII | + | repressed | induced |
| QCR2 | 40 kD subunit II | + | repressed | induced |
| CYC1 | iso-1-cytochrome c | + | repressed | induced |
| SUC2 | invertase | − | repressed | repressed |

TABLE II

Oxygen consumption capacity of Dl1 and DL1HAP yeast cells

| | oxygen consumption nmol/min/mg dry weight | |
|---|---|---|
| | Glucose (4%)-grown cells | Lactate-grown cells |
| DL1 | 9.4 | 88.1 (9.4 × wt Glu) |
| DL1HAP | 18.1 (1.9 × wt Glu) | 86.7 (9.2 × wt Glu) |

TABLE III

Biomass yield.

| strain | $Y_{glu}$ g. dry weight · g$^{-1}$Glu |
|---|---|
| Dl1 | 10.1 |
| DL1HAP | 14.8 |

TABLE IV

Carbon compounds in culture medium during batch growth in fermentors. Data are mean values of several experiments

| strain | ethanol | acetate | glycerol |
|---|---|---|---|
| | mol.L$^{-1}$.g$^{-1}$ dry weight cells | | |
| Dl1 | 79.5 | 1.6 | 10.2 |
| DL1HAP | 49.4 | 3.6 | 2.9 |

TABLE V

Carbon fluxes indicated as percentage mol C of consumed glucose Carbon balance DL1 = 103%, DL1HAP = 108%

| strain | $CO_{2-TCA}$ | ethanol | acetate | glycerol | biomass |
|---|---|---|---|---|---|
| Dl1 | 7.3 | 72.5 | 1.4 | 9.5 | 12.2 |
| DL1HAP | 15.5 | 66.0 | 5.0 | 4.0 | 17.8 |

TABLE VI

Oxygen consumption capacity of industrial strains

| | oxygen consumption nmol/min/mg dry weight | |
|---|---|---|
| | Glucose (4%)-grown cells | Lactate-grown cells |
| DS28911 | 25.3 | ND |
| DS28911-GH2a | 104.0 (4.1 × wt glu) | ND |
| DS28911-TH2a | 75.0 (3.0 × wt glu) | ND |
| DS18332 | 31.5 | 241 (7.7 × wt glu) |
| DS18332-GH1a | 94.5 (3.0 × wt glu) | ND |
| DS18332-TH2a | 70.3 (2.2 × wt glu) | ND |
| DS19806 | 23.8 | ND |
| DS19806-GH1a | 87.2 (3.7 × wt glu) | ND |
| DS19806-TH2a | 65.6 (2.8 × wt glu) | ND |

What is claimed is:

1. A method for preparing a yeast having multiple pathways, wherein the preferred metabolic pathway in the presence of a glucose or sugars giving glucose repression as a carbon source is limited or circumvented, comprising:
transforming the yeast with a nucleic acid construct containing a gene encoding a transcriptional activator for at least one gene encoding an enzyme in one of said pathways under conditions wherein the transcription activator is over expressed causing glucose-repressed genes to derepress or circumvent the repression of one metabolic pathway which is not preferred in the presence of said carbon source and wherein the transcription activator is HAP4 or a functional equivalent or a fragment thereof wherein the molecule still has the same activity as HAP4 in transactivation.

2. A method according to claim 1 whereby the yeast is Saccharomyces.

3. A method according to claim 2 whereby the Saccharomyces is a *Saccharomyces cerevisiae*.

4. A method according to claim 1 whereby the repressed metabolic pathway includes the respiratory or glyconegesis pathway.

5. A method according to claim 1 whereby the pathways for metabolism of the non-preferred carbon sources are activated.

6. A method according to claim 1 whereby the transcriptional activator is provided by introduction into the yeast of a recombinant nucleic acid encoding said activator.

7. A method according to claim 6 whereby said recombinant nucleic acid is an expression vector.

8. A method according to claim 6 whereby the recombinant nucleic acid is derived from the same species as the yeast.

9. A method according to claim 1 whereby the transcriptional activator is constitutively expressed by said yeast.

10. A method according to claim 1 whereby the transcriptional activator is expressed by the yeast upon induction.

11. A method according to claim 10 whereby expression of said activator is induced by the presence of glucose.

12. A method according to claim 1 whereby the yeast comprises a recombinant nucleic acid encoding a protein of interest.

13. A method according to claim 12 whereby said recombinant nucleic acid is an expression vector.

14. A method according to claim 12 whereby said protein of interest is a heterologous protein.

15. A yeast obtained by the method according to claim 1.

16. A yeast according to claim 15 having improve biomass upon culturing.

17. A yeast according to claim 15 showing increased glucose oxidation.

18. A yeast according to claim 15 displaying increased oxidative sugar metabolism.

19. A yeast according to claim 15 displaying reduced production of ethanol.

20. A yeast according to claim 15 which under anaerobic culturing conditions behaves essentially the same as the corresponding unmodified yeast.

* * * * *